(12) United States Patent
Lopes-Virella et al.

(10) Patent No.: US 8,568,995 B2
(45) Date of Patent: Oct. 29, 2013

(54) METHODS FOR ASSESSING MODIFIED LDL IMMUNE COMPLEXES IN SUBJECTS HAVING OR AT RISK OF CORONARY ARTERY DISEASE

(75) Inventors: Maria F. Lopes-Virella, Charleston, SC (US); Gabriel T. Virella, Charleston, SC (US)

(73) Assignees: MUSC Foundation for Research Development, Charleston, SC (US); Department of Veterans Affairs, Washington, DC (US)

( * ) Notice: Subject to any disclaimer, the term of this patent is extended or adjusted under 35 U.S.C. 154(b) by 398 days.

(21) Appl. No.: 12/885,020

(22) Filed: Sep. 17, 2010

(65) Prior Publication Data
US 2011/0124119 A1    May 26, 2011

Related U.S. Application Data

(60) Provisional application No. 61/243,770, filed on Sep. 18, 2009.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/130.1; 424/9.1; 530/300; 530/350

(58) Field of Classification Search
None
See application file for complete search history.

(56) References Cited

PUBLICATIONS

Andersson et al., "Adaptive Immunity and Atherosclerosis," *Clin. Immunol.*, 134(1):33-46, 2010. [Available online Jul. 26, 2009.].
Atchley el al., "Oxidized LDL—anti-oxidized LDL immune complexes and diabetic nephropathy," *Diabetologia*, 45:1562-1571, 2002.
Bevan et al., "Validation of a novel ELISA for measurement of MDA-LDL in human plasma," *Free Radic. Biol. Med.*, 35(5):517-527, 2003.
Hamad et al., "Oxidized LDL immune complexes and oxidized LDL differentially affect the expression of genes involved with inflammation and survival in human U937 monocytic cells," *Atherosclerosis*, 202(2): 394-404, 2009.
Klein et al., "LDL-containing immune complexes in the DCCT/EDIC cohort: associations with lipoprotein subclasses," *J. Diabetes and its Complications*, 25(2): 73-82, 2011. [published online Jun. 4, 2010.].
Lopes-Virella and Virella, "The role of immune and inflammatory processes in the development of macrovascular disease in diabetes," *Frontiers in Bioscience*, 8:s750-768, 2003.
Lopes-Virella et al., "Antibodies to oxidized LDL and LDL-containing immune complexes as risk factors for coronary artery disease in diabetes mellitus," *Clin. Immunol.*, 90(2):165-172, 1999.
Lopes-Virella et al., "Immune complexes containing modified lipoproteins are related to the progression of internal carotid intima-media thickness in patients with type I diabetes," *Atherosclerosis*, 190(2):359-369, 2007.
Lopes-Virella et al., "Risk factors related to inflammation and Endothelial dysfunction in the DCCT/EDIC cohort and their relationship with nephropathy and macrovascular complications," *Diabetes Care*, 31(10):2006-2012 , 2008.
Lopes-Virella et al., "The immunogenicity of modified lipoproteins," *Annals of New York Academy of Sciences*, 1043: 367-378, 2005.
Mironova et al., "Isolation and characterization of human antioxidized LDL autoantibodies," *Arterioscler. Thromb. Vasc. Biol.*, 16:222-229, 1996.
Nicoloff et al., "Circulating immune complexes among diabetic children," *Clinical & Developmental Immunology*, 11 (1):61-66, 2004.
Orchard et al., "Antibodies to oxidized LDL predict coronary artery disease in type 1 diabetes," *Diabetes*, 48(7):1454-1458, 1999.
Saad et al., "Autoimmune oxLDL Immune Complexes activate the classical pathway of complement and induce cytokine production by MonoMac cells and human macrophages," *J. Lipid. Res.*, 47(9):1975-1983, 2006.
Seliger, "Inflammation and dyslipidemia innephropathy: an epidemiologic perspective," *Kidney International* 69 (2): 206-208, 2006.
Virella and Lopes-Virella, "Atherogenesis and the humoral immune response to modified lipoproteins," *Atherosclerosis*, 200(2):239-246, 2008.
Virella and Lopes-Virella, "Lipoprotein Autoantibodies: Measurement and Significance," *Clin. Diag. Lab. Immunol.*, 10:499-505, 2003.
Virella and Tsokos, "Immune Complex Diseases," In: *Medical Immunology*, Virella (Ed.), NY and London: 323-334, 2007.
Virella et al., "Autoimmune response to advanced glycosylation end-products of human LDL," *J. Lipid Res.*, 44:487-493, 2003.
Virella et al., Definition of the immunogenic forms of modified human LDL recognized by human auto-antibodies and by rabbit hyperimmune antibodies, *J. Lipid Res.*,45:1859-1867, 2004.
Virella et al., "Development of capture assays for different modifications of human low density lipoprotein," *Clin. Diagn. Lab. Immunol.*, 12(1):68-75, 2005.
Virella et al., "Distribution of IgM and IgG antibodies to oxidized LDL in immune complexes isolated from patients with type 1 diabetes and its relationship with nephropathy," *Clin. Immunol.*, 127(3):394-400, 2008.
Virella et al., "Immunochemical Characterization of Purified Human Oxidized Low-Density Lipoprotein Antibodies," *Clin. Immunol.*, 95(2):135-144, 2000.
Virella, "Biosynthesis, metabolism and biological properties of immunoglobulins," In: *Medical Immunology* Virella (Ed.), NY and London: 65-72, 2007.
Yishak et al., "Novel predictors of overt nephropathy in subjects with type 1 diabetes. A nested case control study from the Pittsburgh Epidemiology of Diabetes Complications cohort," *Nephrol Dial Transplant* , 21: 93-100, 2006.

(Continued)

*Primary Examiner* — Lisa Cook
(74) *Attorney, Agent, or Firm* — Parker Highlander PLLC

(57) ABSTRACT

The present invention relates to the analysis of modified LDL in the context of immune complexes. In particular, ox-LDL and AGE-LDL are shown to predict the development of coronary artery disease and other micro- and macrovascular disorders, particularly in the context of diabetes.

20 Claims, 5 Drawing Sheets

(56) References Cited

PUBLICATIONS

Yla-Herttuala et al., "Evidence for the presence of oxidatively modified low density lipoprotein in atherosclerotic lesions of rabbit and man," *J. Clin. Invest.*, 84:1086-1095, 1989.

Yla-Herttuala et al., "Rabbit and human atherosclerotic leisons contain IgG that recognizes epitopes of oxidized LDL," *Arterioscler. Thromb. Vasc. Biol.*, 14:32-40, 1994.

Lopes-Virella & Virella, "Clinical significance of the humoral immune response to modified LDL," *Clinical Immunology*, 134(1): 55-65, 2010.

Lopes-Virella et al., "Levels of oxidized LDL and advanced glycation end products—modified LDL in circulating immune complexes are strongly associated with increased levels of carotid intima-media thickness and its progression in type 1 diabetes," *Diabetes*, 60: 582-589, 2011.

Lopes-Virella et al., "Oxidized LDL immune complexes and coronary artery calcification in type 1 diabetes," *Atherosclerosis*, 214:462-467, 2011.

METHODS FOR ASSESSING MODIFIED LDL IMMUNE COMPLEXES IN SUBJECTS HAVING OR AT RISK OF CORONARY ARTERY DISEASE

This application claims benefit of priority to U.S. Provisional Application Ser. No. 61/243,770, filed Sep. 18, 2009, the entire contents of which are hereby incorporated by reference.

This invention was made with government support under grant numbers P01 HL055782 and R01 DK081352 awarded by the National Institutes of Health, and a grant from the Veterans' Administration BLR&D. The United States government has certain rights in the invention.

BACKGROUND OF THE INVENTION

I. Field of the Invention

The invention relates to the field of molecular biology, particularly to the examination of modified LDL-immune complexes to assess human diseases including type 1 diabetes and coronary heart disease, and response to therapies therefor.

II. Related Art

In the recent decades, it has been established that atherosclerosis has a strong chronic inflammatory component (Libby, 2002; Ross, 1999; Steinberg, 2002). Under this perspective, a key issue is the definition of factors that may trigger and perpetuate the inflammatory reaction. In a multifactorial disease such as atherosclerosis, many candidates have emerged, but the understanding of their relative roles is still very incomplete. However, it is clear that modified forms of LDL are major factors in the pathogenesis of atherosclerosis. Oxidized LDL (oxLDL) has been the object of multiple studies pointing to its capacity to trigger proinflammatory events (Drake et al., 1991; Kusuhara et al., 1997; Liao et al., 1991; Quinn et al., 1987; Yla-Herttuala, 1991). This proinflammatory activity of oxLDL has been linked to some of the pathways associated with innate immunity (Drake et al., 1991; Liao et al., 1991; Terkeltaub et al., 1994; Hazen, 2008), but the involvement of modified LDL in pro-inflammatory immunological pathways is not limited to innate immunity pathways. There is strong evidence suggesting that adaptive cell-mediated immunity pathways are also involved in the pathogenesis of atherosclerosis (Virella and Lopes-Virella, 2008; Andersson et al., 2009). T cell activation, in turn, appears to be linked to LDL modification, because peptides derived from oxidized LDL (oxLDL) have been shown to be recognized by T cells (Stemme et al., 1995). However, the strongest link between modified LDL and innate immunity involves the activation of the humoral immune system.

Studies previously performed by the inventors examining the role of modified LDL immune complexes (mLDL-IC) in the development of cardiovascular disease in T1D included a prospective study involving 98 diabetic subjects recruited as part of the Pittsburgh EDC study that showed that modified LDL-IC, using cholesterol as a surrogate marker of modified LDL, and oxLDL antibodies, correlated with the development of coronary artery disease (CAD) over a period of seven years (Lopes-Virella et al., 1999; Orchard et al., 1999). To further evaluate the validity of the hypothesis that modified LDL play a role in the development of cardiovascular complications in T1D, the inventors screened 1050 patients from the DCCT/EDIC cohort for mLDL-IC and evaluated the impact of these IC in progression of internal and common carotid intima-medial thickness (IMT), a surrogate marker for CAD. They found that, after adjustment for age, gender, IMT at year 1, ultrasonography equipment used to measure IMT, DCCT randomization group, smoking, hypertension, HbA1c, logarithm of the albumin excretion rate (AER) and CReactive Protein (CRP) levels, mLDL-IC levels were associated with progression of internal carotid IMT (Mironova et al., 1997). However, the measurements were made using cholesterol as a surrogate marker for modified LDL and using serum samples collected after enrollment of the patients on the EDIC phase of the study, thus several years after enrollment into the DCCT. Furthermore, the samples were collected two years after the first carotid IMT measurement and 2 years before the second measurement, and therefore the predictive value of the IC could not be adequately assessed.

SUMMARY OF THE INVENTION

Thus, in accordance with the present invention, there is provided a method of predicting risk of coronary artery disease (CAD) in a subject comprising (a) providing a modified low density lipoprotein-immune complex (mod-LDL-IC)-containing sample from said subject; (b) measuring oxidized-LDL immune complexes (ox-LDL-IC) and/or advanced glycation endproduct-LDL immune complexes (AGE-LDL-IC) in said sample; (c) comparing the amount of ox-LDL-IC and/or AGE-LDL-IC in said sample to a normal standard; and (d) predicting that said subject is at risk of developing CAD where an elevated amount of ox-LDL-IC and/or AGE-LDL-IC as compared to said standard is observed, or predicting that said subject is at not risk of developing CAD based where an elevated amount of ox-LDL-IC and/or AGE-LDL-IC as compared to said standard is not observed. The mod-LDL-IC-containing sample may be serum or plasma.

Measuring may comprise (i) isolating mod-LDL-IC, (ii) separating mod-LDL from antibodies in said mod-LDL-IC, and (iii) determining ox-LDL and/or AGE-LDL from said mod-LDL-IC levels. Isolating mod-LDL-IC may comprise precipitation, such as PEG precipitation. Separating may comprise affinity chromatography of precipitated mod-LDL-IC followed by selective elution of mod-LDL. Determining may comprise capture immunoassay, competitive immunoassay, gas chromatography, mass spectrometry, gel electrophoresis or column chromatography.

The subject may exhibit elevated ox-LDL levels, elevated AGE-LDL levels, both elevated ox-LDL and AGE-LDL levels, or does not exhibit elevated ox-LDL or AGE-LDL levels. The subject may have a family history of CAD, may be male or female, and may be 5 years of age or less, 10 years of age or less, 15 years of age or less or 20 years of age or less. The CAD may be secondary to type 1 diabetes, type 2 diabetes, or to a chronic autoimmune disorder, such as systemic lupus erythematosus or rheumatoid arthritis.

In another embodiment, there is provided a method of predicting risk of developing a micro- and/or macrovascular complication of type 1 diabetes (T1D) in a subject comprising (a) providing a modified low density lipoprotein-immune complex (mod-LDL-IC)-containing sample from said subject; (b) measuring oxidized-LDL immune complexes (ox-LDL-IC) and/or advanced glycation endproduct-LDL immune complexes (AGE-LDL-IC) in said sample; (c) comparing the amount of ox-LDL-IC and/or AGE-LDL-IC in said sample to a normal standard; and (d) predicting that said subject is at risk of developing micro- and/or macrovascular complication where an elevated amount of ox-LDL-IC and/or AGE-LDL-IC as compared to said standard is observed, or predicting that said subject is at not risk of developing micro- and/or macrovascular complication based where an elevated amount of ox-LDL-IC and/or AGE-LDL-IC as compared to said standard is not observed. The mod-LDL-IC-containing sample may be serum or plasma.

Measuring may comprise (i) isolating mod-LDL-IC, (ii) separating mod-LDL from antibodies in said mod-LDL-IC, and (iii) determining ox-LDL and/or AGE-LDL from said mod-LDL-IC levels. Isolating mod-LDL-IC may comprise precipitation, such as PEG precipitation. Separating may comprise affinity chromatography of precipitated mod-LDL-IC followed by selective elution of mod-LDL. Determining may comprise capture immunoassay, competitive immunoassay, gas chromatography, mass spectrometry, gel electrophoresis or column chromatography.

The subject may exhibit elevated ox-LDL levels, elevated AGE-LDL levels, both elevated ox-LDL and AGE-LDL levels, or does not exhibit elevated ox-LDL or AGE-LDL levels. The subject may have a familial history of T1D with micro- and/or macrovascular complications, such as one or more of cardiovascular disease, peripheral vascular disease, neuropathy, retinopathy and/or nephropathy.

In yet another embodiment, there is provided a method of predicting efficacy of a treatment of a type 1 diabetes (T1D) complication in a subject comprising (a) providing a first modified low density lipoprotein-immune complex (mod-LDL-IC)-containing sample from said subject; (b) measuring oxidized-LDL immune complexes (ox-LDL-IC) and/or advanced glycation endproduct-LDL immune complexes (AGE-LDL-IC) in said first sample; (c) treating said subject for said T1D complication; (d) providing a second modified low density lipoprotein-immune complex (mod-LDL-IC)-containing sample from said subject; (e) measuring oxidized-LDL immune complexes (ox-LDL-IC) and/or advanced glycation endproduct-LDL immune complexes (AGE-LDL-IC) in second said sample; (f) comparing the amount of ox-LDL-IC and/or AGE-LDL-IC in said first sample to said second sample; and (g) determining that said treatment is effective when the amount of ox-LDL-IC and/or AGE-LDL-IC in said second sample is reduced as compared to said first sample, or determining that said treatment is not effective when the amount of ox-LDL-IC and/or AGE-LDL-IC in said second sample is not reduced as compared to said first sample. The mod-LDL-IC-containing sample may be serum or plasma.

Measuring may comprise (i) isolating mod-LDL-IC, (ii) separating mod-LDL from antibodies in said mod-LDL-IC, and (iii) determining ox-LDL and/or AGE-LDL from said mod-LDL-IC levels. Isolating mod-LDL-IC may comprise precipitation, such as PEG precipitation. Separating may comprise affinity chromatography of precipitated mod-LDL-IC followed by selective elution of mod-LDL. Determining may comprise capture immunoassay, competitive immunoassay, gas chromatography, mass spectrometry, gel electrophoresis or column chromatography.

The subject may exhibit elevated ox-LDL levels, elevated AGE-LDL levels, both elevated ox-LDL and AGE-LDL levels, or does not exhibit elevated ox-LDL or AGE-LDL levels. The method may further comprise making a decision to continue or discontinue said treatment of said subject, or may further comprise making a decision to provide an additional continued treatment to said subject. The T1D complication may include one or more of cardiovascular disease, peripheral vascular disease, neuropathy, retinopathy and/or nephropathy.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed.

(FIG. 1A) The Quartiles of oxLDL in isolated LDL-IC are 1: 5-89 (mg/L) 2: 90-162, 3: 163-305, 4: 306-1382. Linear Trend Test: Year 1 (F=27.21; P<0.001); Year 6 (F=27.91; P<0.001). (FIG. 1B) The Quartiles of AGE in isolated LDL-IC are 1: 0.15-2.64 (mg/L), 2: 2.65-6.42, 3: 6.43-12.03, 4: 12.17-305.34. Linear Trend Test: Year 1 (F=25.28; P<0.001); Year 6 (F=24.85; P<0.001). (FIG. 1C) The Quartiles of MDA in isolated LDL-IC are 1: 3-43 (mg/L), 2: 44-108, 3: 109-202. 4: 203-1296. Linear Trend Test: Year1 (F=4.59; P=0.033); Year 6 (F=6.39; P=0.012).

Figure 4:
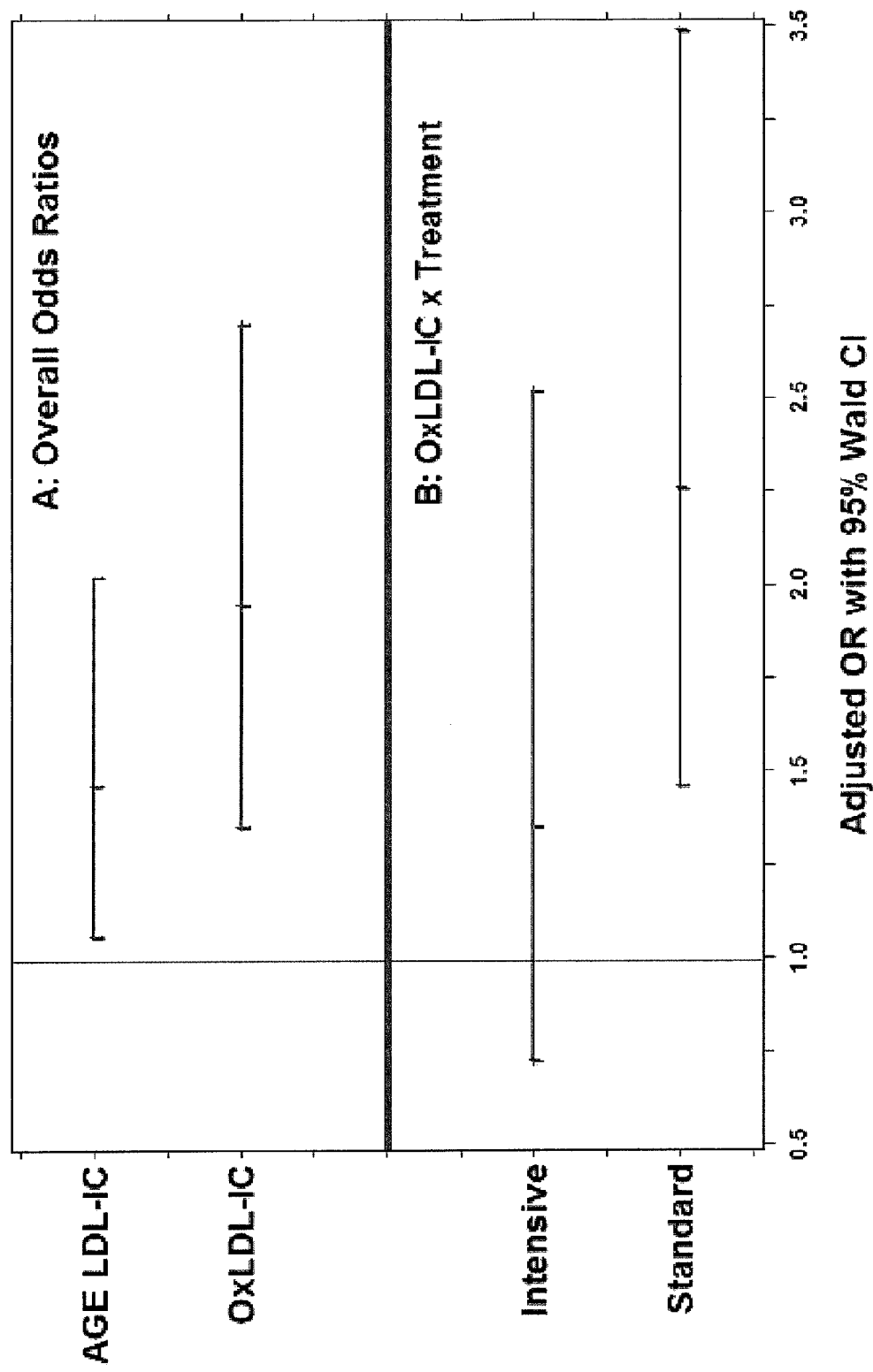

FIGS. 4A-B. Graphic representation of the odds of developing nephropathy with the 95% confidence interval based on a one standard deviation change in the Ox LDL-IC and AGE LDL-IC values. The odds ratios are adjusted for DCCT Treatment Group, Mild Retinopathy at baseline, and HbA1C % at baseline. (FIG. 4A) Adjusted Odds of Nephropathy with 95% CI for 1 Standard Deviation Change in Ox LDL-IC and AGE LDL-IC. The increased odds of nephropathy development with a 1 standard deviation increase in Ox LDL-IC is 1.947 (95% CI 1.354-2.801). The increased odds of nephropathy development with a 1 standard deviation increase in AGE LDL-IC is 1.464 (95% CI 1.059-2.023). (FIG. 4B) Adjusted Odds of Nephropathy with the 95% CI for 1 Standard Deviation change in the Ox LDL-IC values for the standard (Stnd) and Intensive (Int) treatment groups. The odds ratios are adjusted for Mild Retinopathy at baseline, duration of diabetes at DCCT Baseline, LDL at baseline, and HbA1C % at baseline. The increased odds of nephropathy development with a 1 standard deviation increase in Ox LDL-IC for the standard treatment group is 2.260 (95% CI 1.464-3.490) while the odds ratio for the experimental group is 1.355 (95% CI 0.728-2.520).

Figure 5:
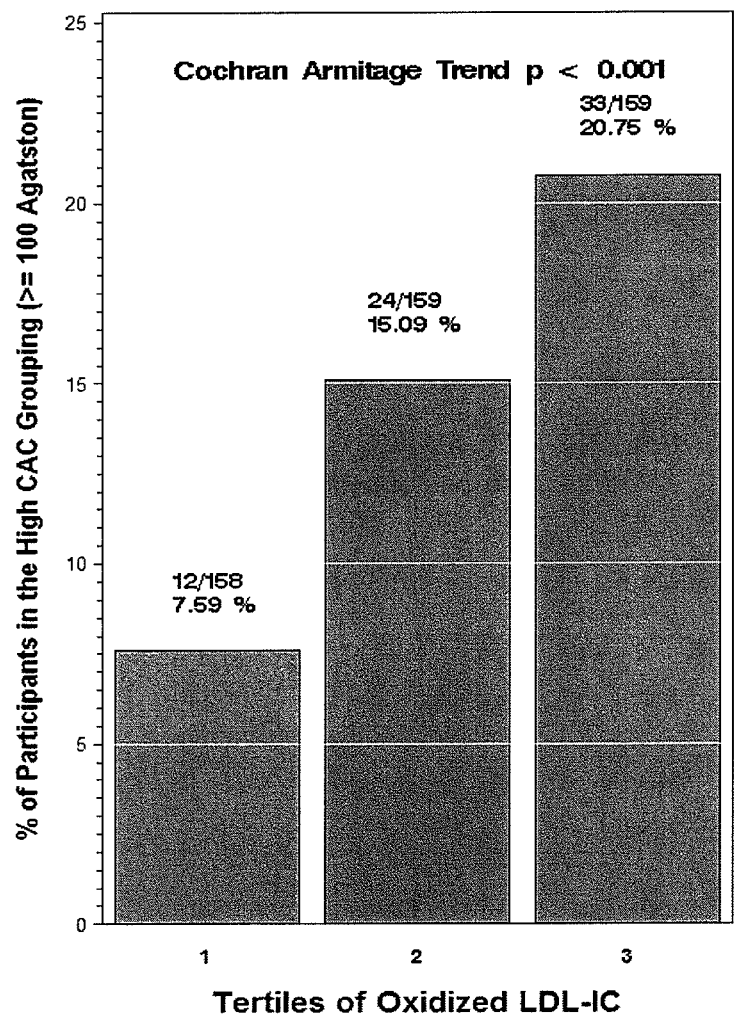

FIG. 5. Incidence of CAC scores (≥100 Agatstons) by tertile of oxidized LDL-Immune Complex. The tertiles of oxLDL-IC are 1: 4-106 (mg/L) 2: 107-246, and 3: 247-1382.

DETAILED DESCRIPTION OF THE INVENTION

The pro-inflammatory properties of immune complexes have been well-characterized for several decades (Virella and Tsokos, 2007). In reality, the pathogenic potential of autoantibodies depends on two main factors: the antibody isotype and the deposition or in situ formation of IC in the extravascular space. Antibodies of the IgG1 and IgG3 isotypes are known to be pro-inflammatory, because of their easy diffusibility across the endothelial barrier and their capacity to activate the complement system by the classical pathway and of interacting with Fcγ receptors in phagocytic cells (Virella and Tsokos, 2007; Virella, 2007). Given that both circulating and complexed human autoantibodies to both oxLDL and AGE-LDL are predominantly IgG of the IgG1 and IgG3 isotypes (Virella and Lopes-Virella, 2003; Virella et al., 2008; Saad et al., 2006; Virella et al., 2000; Virella et al., 2003), it would be fully expected that they could play a pathogenic role in chronic inflammatory processes, such as atherosclerosis. However, this potential has not been clearly supported by previous clinical trials is a consequence of technical difficulties surrounding the measurement of antibodies to modified lipoproteins and the corresponding IC. In either assay, preformed IC interfere with the assays, and any method designed to measure the amounts and characteristics of circulating IC requires isolation of IC followed by dissociation and separation of antigens and antibodies. Antigen measurements have the advantage of identifying the complex of interest because IC of different natures can share antibody isotypes, and the isolation steps are usually non-specific for any given type of circulating IC. The consequence of these limitations is that reliable assays are complex and time-consuming, and both exhibit significant difficulties when the objective is the study of large patient cohorts.

In the present study, the inventors performed specific measurements of the most prevalent IC in type 1 diabetes (oxLDL-IC, AGE-LDL-IC and MDA-LDL-IC) in serum samples collected from the DCCT/EDIC cohort at the time of enrollment and randomization into the DCCT trial, and determined their value compared to other conventional risk factors (e.g., lipids, lipoproteins, HbA1c and albumin excretion rate to predict the development of CAD, as assessed by two measurements of carotid IMT performed approximately 10 and 15 years after the samples were collected). This study has shown for the first time that high levels of oxLDL and AGE-LDL IC, even measured at very young age and when the patient is free of macrovascular disease, are strongly predictive of accelerate intima-media thickening over a period of 6-12 years (first carotid IMT measurement) or 11-17 years (second carotid IMT measurement), the predictive odds for these IC largely exceed classical predictive factors such as age, gender, smoking, AER and LDL-cholesterol concentration. Evidently, the measurement of modified lipoproteins in IC isolated from peripheral blood is only a surrogate marker for the formation of extravascular IC of the same nature, but its is a very reasonable surrogate marker because both modified LDL and the corresponding antibodies have been identified in atheromatous lesions (Yla-Herttuala et al., 1989; Yla-Herttuala et al., 1994).

Interestingly, the levels of MDA-LDL-IC are not as predictive of CAD, as assessed by carotid IMT. This could be a reflection of the fact that MDA-LDL prepared in the laboratory is structurally different from oxLDL generated in vivo, while copper-oxidized LDL is structurally closer. Inhibition studies performed with IgG oxLDL antibodies purified from precipitated IC showed that the reactivity with immobilized copperoxidized LDL was only inhibited to a small extent with MDA-LDL (Virella et al., 2004), meaning that oxLDL contains additional epitopes besides MDA-lysine. It seems clear that the non-MDA epitopes of oxLDL are predominantly involved in the formation of pathogenic IC, and therefore, are responsible for a strong predictive power concerning the development of CAD.

Whether the strong predictive power of oxLDL-IC and AGE-LDL-IC in the development of CAD is unique to T1D cannot be concluded from this study. On one hand, the same predominance of IgG1 and IgG3 oxLDL antibodies has been found in non-diabetic patients and healthy controls (Mironova et al., 1996). On the other, patients with T1D have a complex constellation of genetic factors associated with their autoimmune disease that could very well have an influence on the magnitude of their autoimmune response to modified lipoproteins. It is, however, quite clear that the measurement of circulating oxLDL-IC or AGE-LDL-IC will be very important to identify subjects with T1D at high risk for developing CAD even at very young age and before the disease is manifested. This finding may help to prevent or delay the development of macrovascular complications in T1D. These and other aspects of the invention are described in detail below.

I. CORONARY ARTERY DISEASE (CAD)

Coronary artery disease (CAD), or atherosclerotic heart disease, is the end result of the accumulation of atheromatous plaques within the walls of the coronary arteries that supply the myocardium (the muscle of the heart) with oxygen and nutrients. It is sometimes also called coronary heart disease (CHD), but although CAD is the most common cause of CHD, it is not the only cause. CAD is the leading cause of death worldwide. While the symptoms and signs of coronary artery disease are noted in the advanced state of disease, most individuals with coronary artery disease show no evidence of disease for decades as the disease progresses before the first onset of symptoms, often a "sudden" heart attack, finally arises. After decades of progression, some of these atheromatous plaques may rupture and (along with the activation of the blood clotting system) start limiting blood flow to the heart muscle. The disease is the most common cause of sudden death, and is also the most common reason for death of men and women over 20 years of age. According to present trends in the United States, half of healthy 40-year-old males will develop CAD in the future, and one in three healthy 40-year-old women.

As the degree of coronary artery disease progresses, there may be near-complete obstruction of the lumen of the coronary artery, severely restricting the flow of oxygen-carrying blood to the myocardium. Individuals with this degree of coronary artery disease typically have suffered from one or more myocardial infarctions (heart attacks), and may have signs and symptoms of chronic coronary ischemia, including symptoms of angina at rest and flash pulmonary edema. An individual may develop a rupture of an atheromatous plaque at any stage of the spectrum of coronary artery disease. The acute rupture of a plaque may lead to an acute myocardial infarction (heart attack).

Limitation of blood flow to the heart causes ischemia (cell starvation secondary to a lack of oxygen) of the myocardial cells. Myocardial cells may die from lack of oxygen and this is called a myocardial infarction (commonly called a heart attack). It leads to heart muscle damage, heart muscle death and later myocardial scarring without heart muscle regrowth. Chronic high-grade stenosis of the coronary arteries can induce transient ischemia which leads to the induction of a ventricular arrhythmia, with may terminate into ventricular fibrillation leading to death.

Myocardial infarction usually results from the sudden occlusion of a coronary artery when a plaque ruptures, activating the clotting system and atheroma-clot interaction fills the lumen of the artery to the point of sudden closure. The narrowing of the lumen of the heart artery before sudden closure is often not severe, according to clinical research completed in the late 1990s and using IVUS examinations within 6 months prior to a heart attack. The events leading up to plaque rupture are not understood despite many theories. Myocardial infarction is almost never caused by temporary spasm of the artery wall occluding the lumen, a condition also associated with atheromatous plaque and CAD.

CAD is associated with smoking, diabetes, and hypertension. A family history of early CAD is one of the less important predictors of CAD. Most of the familial association of coronary artery disease are related to common dietary habits. Screening for CAD includes evaluating high-density and low-density lipoprotein (cholesterol) levels and triglyceride levels. Despite much press, most of the alternative risk factors including homocysteine, C-reactive protein (CRP), Lipoprotein (a), coronary calcium and more sophisticated lipid analysis have added little if any additional value to the conventional risk factors of smoking, diabetes and hypertension.

Angina (chest pain) that occurs regularly with activity, after heavy meals, or at other predictable times is termed stable angina and is associated with high grade narrowings of the heart arteries. The symptoms of angina are often treated with betablocker therapy such as metoprolol or atenolol. Nitrate preparations such as nitroglycerin, which come in short-acting and long-acting forms are also effective in relieving symptoms but are not known to reduce the chances of future heart attacks. Many other more effective treatments, especially of the underlying atheromatous disease, have been developed. Angina that changes in intensity, character or frequency is termed unstable. Unstable angina may precede myocardial infarction, and requires urgent medical attention. It may be treated with oxygen, intravenous nitroglycerin, and aspirin. Interventional procedures such as angioplasty may be done.

Typically, coronary artery disease occurs when part of the smooth, elastic lining inside a coronary artery (the arteries that supply blood to the heart muscle) develops atherosclerosis. With atherosclerosis, the artery's lining becomes hardened, stiffened, and swollen with material such as calcium deposits, fatty deposits, and abnormal inflammatory cells, which form a plaque. Deposits of calcium phosphates (hydroxyapatites) in the muscular layer of the blood vessels appear to play not only a significant role in stiffening arteries, but also for the induction of an early phase of coronary arteriosclerosis. This can be seen in a so-called metatstatic mechanism of calcification as it occurs in chronic kidney disease and haemodialysis (Rainer Liedtke, 2008). Although these patients suffer from a kidney dysfunction, almost fifty percent of them die due to coronary artery disease. Patients with coronary artery disease might have just one or two plaques, or might have dozens distributed throughout their coronary arteries.

The following are confirmed independent risk factors for the development of CAD: hypercholesterolemia (specifically, serum LDL concentrations), smoking, hypertension, (high systolic pressure seems to be most significant in this regard), hyperglycemia (due to diabetes mellitus or otherwise), and hemostatic factors (high levels of fibrinogen and coagulation factor VII), hereditary differences in such diverse aspects as lipoprotein structure and that of their associated receptors, homocysteine processing/metabolism, etc., and high levels of Lp(a). Significant, but indirect risk factors include: lack of exercise, stress, diet rich in saturated fats, diet low in antioxidants, obesity, and age (men over 60; women over 65).

CAD has always been difficult to diagnose without the use of invasive or stressful activities. The development of the Multifunction Cardiogram (MCG) has changed the way CAD is diagnosed. The MCG consists of a 2 lead resting EKG signal is transformed into a mathematical model and compared against tens of thousands of clinical trials to diagnose a patient with an objective severity score, as well as secondary and tertiary results about the patients condition. The results from MCG tests have been validated in 8 clinical trials which resulted in a database of over 50,000 patients where the system has demonstrated accuracy comparable to coronary angiography (90% overall sensitivity, 85% specificity). This level of accuracy comes from the application of advanced techniques in signal processing and systems analysis combined with a large scale clinical database which allows MCG to provide quantitative, evidence-based results to assist physicians in reaching a diagnosis. The MCG has also been awarded a Category III CPT code by the American Medical Association in the July 2009 CPT update.

Coronary artery disease is the most common form of heart disease in the Western world. Prevention centers on the modifiable risk factors, which include decreasing cholesterol levels, addressing obesity and hypertension, avoiding a sedentary lifestyle, making healthy dietary choices, and stopping smoking. There is some evidence that lowering homocysteine levels may contribute to more heart attacks (NORVIT trial). In diabetes mellitus, there is little evidence that very tight blood sugar control actually improves cardiac risk, although improved sugar control appears to decrease other undesirable problems like kidney failure and blindness. Some recommend a diet rich in omega-3 fatty acids and vitamin C.

An increasingly growing number of other physiological markers and homeostatic mechanisms are currently under scientific investigation. Patients with CAD and those trying to prevent CAD are advised to avoid fats that are readily oxidized (e.g., saturated fats and trans-fats), limit carbohydrates and processed sugars to reduce production of low density lipoproteins, triacylglycerol and apolipoprotein-B. It is also important to keep blood pressure normal, exercise and stop smoking. These measures reduces the development of heart attacks. Recent studies have shown that dramatic reduction in LDL levels can cause regression of coronary artery disease in as many as ⅔ of patients after just one year of sustained treatment. Menaquinone (Vitamin K2), but not phylloquinone (Vitamin K1), intake is associated with reduced risk of CAD mortality, all-cause mortality and severe aortic calcification.

It has been suggested that coronary artery disease is partially reversible using an intense dietary regimen coupled with regular cardio exercise. Vegetarians have been shown to have a 24% reduced risk of dying of heart disease. The consumption of trans fat (commonly found in hydrogenated products such as margarine) has been shown to cause the development of endothelial dysfunction, a precursor to atherosclerosis. The consumption of trans fatty acids has been shown to increase the risk of coronary artery disease. Foods containing fiber, potassium, nitric oxide (in green leafy vegetables), monounsaturated fat, polyunsaturated fat, saponins, or lecithin are said to lower cholesterol levels. Foods high in grease, salt, trans fat, or saturated fat are said to raise cholesterol levels.

II. CAD SECONDARY TO OTHER DISEASES

A. Diabetes

Diabetes mellitus is a condition in which the body does not produce enough, or properly respond to, insulin, a hormone produced in the pancreas. Insulin enables cells to absorb glucose in order to turn it into energy. In diabetes, the body either fails to properly respond to its own insulin, does not make enough insulin, or both. This causes glucose to accumulate in the blood, often leading to various complications.

Type 1 diabetes mellitus is characterized by loss of the insulin-producing beta cells of the islets of Langerhans in the pancreas leading to a deficiency of insulin. This type of diabetes can be further classified as immune-mediated or idiopathic. The majority of type 1 diabetes is of the immune-mediated nature, where beta cell loss is a T-cell mediated autoimmune attack. There is no known preventive measure which can be taken against type 1 diabetes, which contain approximately 10% of diabetes mellitus cases in North America and Europe (though this varies by geographical location). Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

The classical symptoms are polyuria and polydipsia which are, respectively, frequent urination and increased thirst and consequent increased fluid intake. Symptoms may develop quite rapidly (weeks or months) in type 1 diabetes, particularly in children. However, in type 2 diabetes symptoms usually develop much more slowly and may be subtle or completely absent. Type 1 diabetes may also cause a rapid yet significant weight loss (despite normal or even increased eating) and irreducible mental fatigue. All of these symptoms except weight loss can also manifest in type 2 diabetes in patients whose diabetes is poorly controlled, although unexplained weight loss may be experienced at the onset of the disease. Final diagnosis is made by measuring the blood glucose concentration.

Prolonged high blood glucose causes glucose absorption, which leads to changes in the shape of the lenses of the eyes, resulting in vision changes; sustained sensible glucose control usually returns the lens to its original shape. Blurred vision is a common complaint leading to a diabetes diagnosis; type 1 should always be suspected in cases of rapid vision change, whereas with type 2 change is generally more gradual, but should still be suspected.

Various hereditary conditions may feature diabetes, for example myotonic dystrophy and Friedreich's ataxia. Wolfram's syndrome is an autosomal recessive neurodegenerative disorder that first becomes evident in childhood. It consists of diabetes insipidus, diabetes mellitus, optic atrophy, and deafness, hence the acronym DIDMOAD.

Diabetes mellitus is characterized by recurrent or persistent hyperglycemia, and is diagnosed by demonstrating fasting plasma glucose level at or above 126 mg/dL (7.0 mmol/L), plasma at or above 200 mg/dL (11.1 mmol/L) two hours after a 75 g oral glucose load as in a glucose tolerance test, and/or symptoms of hyperglycemia and casual plasma glucose at or above 200 mg/dL (11.1 mmol/L). A positive result, in the absence of unequivocal hyperglycemia, should be confirmed by a repeat of any of the above-listed methods on a different day. Most physicians prefer to measure a fasting glucose level because of the ease of measurement and the considerable time commitment of formal glucose tolerance testing, which takes two hours to complete and offers no prognostic advantage over the fasting test. According to the current definition, two fasting glucose measurements above 126 mg/dL (7.0 mmol/L) is considered diagnostic for diabetes mellitus. Patients with fasting glucose levels from 100 to 125 mg/dL (6.1 and 7.0 mmol/L) are considered to have impaired fasting glucose. Patients with plasma glucose at or above 140 mg/dL or 7.8 mmol/L, but not over 200, two hours after a 75 g oral glucose load are considered to have impaired glucose tolerance. Of these two pre-diabetic states, the latter in particular is a major risk factor for progression to full-blown diabetes mellitus as well as cardiovascular disease.

While not used for diagnosis, an elevated level of glucose irreversibly bound to hemoglobin (termed glycosylated hemoglobin or HbA1c) of 6.0% or higher (the 2003 revised U.S. standard) is considered abnormal by most labs; HbA1c is primarily used as a treatment-tracking test reflecting average blood glucose levels over the preceding 90 days (approximately) which is the average lifetime of red blood cells which contain hemoglobin in most patients. However, some physicians may order this test at the time of diagnosis to track changes over time. The current recommended goal for HbA1c in patients with diabetes is 6.5%.

Chronic elevation of blood glucose level leads to damage of blood vessels (angiopathy). The endothelial cells lining the blood vessels take in more glucose than normal, since they don't depend on insulin. They then form more surface glycoproteins than normal, and cause the basement membrane to grow thicker and weaker. In diabetes, the resulting problems are grouped under "microvascular disease" (due to damage to small blood vessels) and "macrovascular disease" (due to damage to the arteries).

However, some research challenges the theory of hyperglycemia as the cause of diabetic complications. The fact that 40% of diabetics who carefully control their blood sugar nevertheless develop neuropathy, and that some of those with good blood sugar control still develop nephropathy, requires explanation. It has been discovered that the serum of diabetics with neuropathy is toxic to nerves even if its blood sugar content is normal. Recent research suggests that in T1D, the continuing autoimmune immune disease which initially destroyed the β cells of the pancreas may also cause retinopathy, neuropathy, and nephropathy. One researcher has even suggested that retinopathy may be better treated by drugs to suppress the abnormal immune system of diabetics than by blood sugar control. The familial clustering of the degree and type of diabetic complications indicates that genetics may also play a role in causing complications such as diabetic retinopathy and nephropathy. Non-diabetic offspring of type 2 diabetics have been found to have increased arterial stiffness and neuropathy despite normal blood glucose levels, and elevated enzyme levels associated with diabetic renal disease have been found in non-diabetic first-degree relatives of diabetics. Even rapid tightening of blood glucose levels has been shown to worsen rather than improve diabetic complications, though it has usually been held that complications would improve over time with more normal blood sugar, provided this could be maintained. However, one study continued for 41 months found that the initial worsening of complications from improved glucose control was not followed by the expected improvement in the complications.

The damage to small blood vessels leads to a microangiopathy, which can cause one or more of the following: diabetic retinopathy, diabetic neuropathy, diabetic amyotrophy, diabetic nephropathy, diabetic cardiomyopathy, coronary artery disease, stroke (mainly the ischemic type), peripheral vascular disease, diabetic myonecrosis, diabetic foot, carotid artery stenosis and diabetic encephalopathy.

B. Inflammatory/Autoimmune Disease

The following autoimmune/inflammatory diseases may exhibit a CAD component and thus many be subject to diagnosis/treatment according to the present invention: rheumatoid arthritis, Sjögren's syndrome, systemic lupus erythematosus, chronic leukocytic leukemia, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure.

III. LDL, MODIFIED LDL'S AND MOD-LDL IMMUNE COMPLEXES

A. LDL

Low-density lipoprotein (LDL) is a type of lipoprotein that transports cholesterol and triglycerides from the liver to peripheral tissues. LDL is one of the five major groups of lipoproteins; these groups include chylomicrons, very low-density lipoprotein (VLDL), intermediate-density lipoprotein (IDL), low-density lipoprotein, and high-density lipoprotein (HDL), although some alternative organizational schemes have been proposed. Like all lipoproteins, LDL enables fats and cholesterol to move within the water-based solution of the blood stream. LDL also regulates cholesterol synthesis at these sites.

Each native LDL particle contains a single apolipoprotein B-100 molecule (Apo B-100, a protein with 4536 amino acid residues), which circulates the fatty acids, keeping them soluble in the aqueous environment. In addition, LDL has a highly-hydrophobic core consisting of polyunsaturated fatty acid known as linoleate and about 1500 esterified cholesterol molecules. This core is surrounded by a shell of phospholipids and unesterified cholesterol, as well as a single copy of B-100 large protein (514 kD). LDL particles are approximately 22 nm in diameter and have a mass of about 3 million daltons, but since LDL particles contain a changing number of fatty acids, they actually have a mass and size distribution.

LDL particles vary in size and density, and studies have shown that a pattern that has more small dense LDL particles—called "pattern B"—equates to a higher risk factor for coronary heart disease (CHD) than does a pattern with more of the larger and less dense LDL particles ("pattern A"). This is because the smaller particles are more easily able to penetrate the endothelium. "Pattern I," meaning "intermediate," indicates that most LDL particles are very close in size to the normal gaps in the endothelium (26 nm). The correspondence between pattern B and CHD has been suggested by some in the medical community to be stronger than the correspondence between the LDL number measured in the standard lipid profile test. Tests to measure these LDL subtype patterns have been more expensive and not widely available, so the common lipid profile test has been used more commonly. There has also been noted a correspondence between higher triglyceride levels and higher levels of smaller, denser LDL particles and alternately lower triglyceride levels and higher levels of the larger, less dense LDL.

When a cell requires cholesterol, it synthesizes the necessary LDL receptors, and inserts them into the plasma membrane. The LDL receptors diffuse freely until they associate with clathrin-coated pits. LDL particles in the blood stream bind to these extracellular LDL receptors. The clathrin-coated pits then form vesicles that are endocytosed into the cell. After the clathrin coat is shed, the vesicles deliver the LDL and their receptors to early endosomes, onto late endosomes to lysosomes. Here the cholesterol esters in the LDL are hydrolysed. The LDL receptors are recycled back to the plasma membrane.

Because LDLs transport cholesterol to the arteries and can be retained there by arterial proteoglycans starting the formation of plaques, increased levels are associated with atherosclerosis, and thus heart attack, stroke, and peripheral vascular disease. For this reason, cholesterol inside LDL lipoproteins is often called "bad" cholesterol. This is a misnomer. The cholesterol transported on LDL is the same as cholesterol transported on other lipoprotein particles. The cholesterol itself is not bad; rather, it is how and where the cholesterol is being transported, and in what amounts over time, that causes adverse effects.

Increasing evidence has revealed that the concentration and size of the LDL particles more powerfully relates to the degree of atherosclerosis progression than the concentration of cholesterol contained within all the LDL particles. The healthiest pattern, though relatively rare, is to have small numbers of large LDL particles and no small particles. Having small LDL particles, though common, is an unhealthy pattern; high concentrations of small LDL particles (even though potentially carrying the same total cholesterol content as a low concentration of large particles) correlates with much faster growth of atheroma, progression of atherosclerosis and earlier and more severe cardiovascular disease events and death.

LDL is formed as VLDL lipoproteins lose triglyceride through the action of lipoprotein lipase (LPL) and become smaller and denser, containing a higher proportion of cholesterol. A hereditary form of high LDL is familial hypercholesterolemia (FH). Increased LDL is termed hyperlipoproteinemia type II (after the dated Fredrickson classification). LDL poses a risk for cardiovascular disease when it invades the endothelium and becomes oxidized, since the oxidized form is more easily retained by the proteoglycans. A complex set of biochemical reactions regulates the oxidation of LDL, chiefly stimulated by presence of free radicals in the endothelium. Nitric oxide down-regulates this oxidation process catalyzed by L-arginine. In a corresponding manner, when there are high levels of asymmetric dimethylarginine in the endothelium, production of nitric oxide is inhibited and more LDL oxidation occurs.

The use of statins (HMG-CoA reductase inhibitors) is effective against high levels of LDL cholesterol. Statins inhibit the enzyme HMG-CoA reductase in the liver, the rate-limiting step of cholesterol synthesis. To compensate for the decreased cholesterol availability, synthesis of LDL receptors is increased, resulting in an increased clearance of LDL from the blood.

Niacin ($B_3$), lowers LDL by selectively inhibiting hepatic diacyglycerol acyltransferase 2, reducing triglyceride synthesis and VLDL secretion through a receptor HM74 and HM74A or GPR109A.

Tocotrienols, especially δ- and γ-tocotrienols, have been shown to be effective nutritional agents to treat high cholesterol in recent research programs. In particular, γ-tocotrienol appears to act on a specific enzyme called 3-hydroxy-3-methylglutaryl-coenzyme A reductase (HMG-CoA reductase) and suppresses the production of this enzyme, which results in less cholesterol being manufactured by liver cells. This decrease in hepatic (liver) LDL levels causes hepatic LDL receptor up-regulation, further decreasing plasma LDL levels as it is taken in by the liver.

Insulin induces HMG-CoA reductase activity, whereas glucagon downregulates it. While glucagon production is stimulated by dietary protein ingestion, insulin production is stimulated by dietary carbohydrate. The rise of insulin is, in general, determined by the digestion of carbohydrates into glucose and subsequent increase in serum glucose levels. Glucagon levels are very low when insulin levels are high.

A ketogenic diet may have similar response to taking niacin (lowered LDL and increased HDL) through beta-hydroxybutyrate, a ketone body, coupling the niacin receptor (HM74A). Lowering the blood lipid concentration of triglycerides helps lower the amount of LDL, because VLDL gets converted in the bloodstream into LDL. Fructose, a component of sucrose as well as high-fructose corn syrup, upregulates hepatic VLDL synthesis. Because LDL appears to be harmless until oxidized by free radicals, it is postulated that ingesting antioxidants and minimizing free radical exposure may reduce LDL's contribution to atherosclerosis, though results are not conclusive.

Chemical measures of lipid concentration have long been the most-used clinical measurement, not because they have the best correlation with individual outcome, but because these lab methods are less expensive and more widely available. However, there is increasing evidence and recognition of the value of more sophisticated measurements. To be specific, LDL particle number (concentration), and to a lesser extent size, have shown much tighter correlation with atherosclerotic progression and cardiovascular events than is obtained using chemical measures of total LDL concentration contained within the particles. LDL cholesterol concentration can be low, yet LDL particle number high and cardiovascular events rates are high. Also, LDL cholesterol concentration can be relatively high, yet LDL particle number low and cardiovascular events are also low. If LDL particle concentration is tracked against event rates, many other statistical correlates of cardiovascular events, such as diabetes mellitus, obesity, and smoking, lose much of their additional predictive power.

In the USA, the American Heart Association, NIH, and NCEP provide a set of guidelines for fasting LDL-Cholesterol levels, estimated or measured, and risk for heart disease. As of 2003, these guidelines were:

| Level (mg/dL) | Level (mmol/L) | Interpretation |
| --- | --- | --- |
| <100 | <2.6 | Optimal LDL cholesterol, corresponding to reduced, but not zero, risk for heart disease |
| 100 to 129 | 2.6 to 3.3 | Near optimal LDL level |
| 130 to 159 | 3.3 to 4.1 | Borderline high LDL level |
| 160 to 189 | 4.1 to 4.9 | High LDL level |
| >190 | >4.9 | Very high LDL level, corresponding to highest increased risk of heart disease |

These guidelines were based on a goal of presumably decreasing death rates from cardiovascular disease to less than 2% to 3% per year or less than 20% to 30% every 10 years. Note that 100 is not considered optimal; less than 100 is optimal, though it is unspecified how much less.

Over time, with more clinical research, these recommended levels keep being reduced because LDL reduction, including to abnormally low levels, has been the most effective strategy for reducing cardiovascular death rates in large double blind, randomized clinical trials; far more effective than coronary angioplasty/stenting or bypass surgery.

For instance, for people with known atherosclerosis diseases, the 2004 updated American Heart Association, NIH and NCEP recommendations are for LDL levels to be lowered to less than 70 mg/dL, unspecified how much lower. It has been estimated from the results of multiple human pharmacologic LDL lowering trials that LDL should be lowered to about 50 to reduce cardiovascular event rates to near zero. For reference, from longitudinal population studies following progression of atherosclerosis-related behaviors from early childhood into adulthood, it has been discovered that the usual LDL in childhood, before the development of fatty streaks, is about 35 mg/dL.

B. Modified LDL

As discussed above, unmodified LDL is not pro-atherogenic. Rather, it is the modified forms of LDL that induce autoantibodies and contribute to atherosclerosis and CAD. A first form of modified LDL mentioned is oxidized LDL, referred to herein as ox-LDL. A second form is glycooxidized (advanced glycosylation endproducts) LDL, or AGE-LDL. A third form is malondialdehyde-modified LDL or MAD-LDL.

LDL oxidation affects both the lipid and protein components of LDL. Reactive aldehyde products formed during oxidation of polyunsaturated fatty acids, such as MDA and HNEmalondialdehyde (HNE-MDA) and hydroxynonenal (HNE), are capable of attaching covalently to the ε-amino groups of lysine residues of ApoB (Terkeltaub et al., 1994; Steinbrecher et al., 1984; Steinbrecher, 1987). These modifications are present in oxLDL as well as in LDL isolated from atherosclerotic plaques, which reacts with monoclonal antibodies produced in guinea pigs against MDA and HNE-lysine (Terkeltaub et al., 1994). It has also been shown that myeloperoxidase (MPO)-induced modifications are immunogenic and the resulting antibodies recognize lipopoproteins deposited in atherosclerotic lesions. Human autoantibodies reacting with oxLDL have also been well-characterized (Eckel et al., 2002; Game et al., 2003; Binder et al., 2002). MDA-lysine and MPO-derived epitopes have been suggested as predominantly involved in the induction of human antibodies (Anderson et al., 2002; Palinski et al., 1989).

Detailed investigations have also been carried out with AGE-modified LDL. Advanced glycosylation involves a chain of chemical reactions that starts with the non-enzymatic addition of reducing sugars to protein amino groups (Schiff base, Amadori adducts). If the half-life of a protein is sufficiently long, additional reactions take place leading to the formation of a heterogeneous family of sugar-amino acid adducts (AGE) (Lopes-Virella et al., 2005). LDL, like most plasma proteins, is susceptible to AGE modification (Requena et al., 1997). AGE-modified proteins are immunogenic (Schmidt et al., 1995) and the corresponding antibodies raised in laboratory animals have been used for the detection of AGE-modified proteins in serum and tissues (Ikeda et al., 1998; Onorato et al., 1998). In humans, AGE-LDL antibodies have been purified from sera with high antibody titers and characterized as far as isotype distribution, avidity, and specificity (Nakamura et al., 1993). Of the two best characterized modifications of AGE proteins, $N^\epsilon$(carboxymethyl)lysine (CML) and $N^\epsilon$(carboxyethyl)lysine (CEL), CML seems to be the most immunogenic, but these data suggest that other epitopes expressed in AGE-LDL are immunodominant relatively to CML (Anderson et al., 2002).

C. LDL Immune Complexes

Most forms of modified LDL are immunogenic and induce the formation of autoantibodies in humans Virella and Lopes-Virella, 2003; Virella et al., 2004). A direct consequence of autoantibody synthesis is the formation of antigen-antibody immune complexes ("IC"). detectable both in serum 11 and in the atheromatous plaque, where both oxLDL and oxLDL antibodies have been found (Yla-Herttuala et al., 1989; Yla-Herttuala et al., 1994). The antibodies present as part of circulating IC isolated from subjects with type 1 diabetes (T1D) are predominantly IgG of the pro-inflammatory subclasses 1 and 3 (Virella et al., 2008), and these auto-antibodies preferentially recognize oxLDL, MDA-LDL, and AGE-LDL from a large battery of tested LDL modifications (unpublished results). In patients with T1D, more than 90% of modified LDL circulated as soluble IC, not free, as previously shown. Only traces of modified lipoproteins were captured in the serum after removal of immune complexes (Virella et al., 2005). In vitro studies have demonstrated that oxLDL-IC have pro-atherogenic and pro-inflammatory properties that greatly exceed those of oxLDL (Saad et al., 2006).

IV. DIAGNOSTICS

A. Separation of Modified LDL from Serum and Plasma

Modified LDL (mod-LDL) are found almost completely in the form of LDL immune complexes in serum and plasma. Thus, measurement of mod-LDL requires isolation of LDL-IC. The present invention can utilize polyethylene glycol (PEG) precipitation of LDL-IC for the isolation of mod-LDL, followed by column chromatography using a protein G column that binds IC through the antibody moiety. Subsequent to binding of IC, mod-LDL can be released from the antibodies bound to the column by treatments that disrupt the antibody-mod-LDL interaction while not disturbing the binding of protein G to the antibody.

B. Immunodetection of Modified LDL

Accordingly, in one embodiment of the present invention, a method for predicting risk of CAD or predicting efficacy of a therapy for CAD is provided. Such methods may rely on the immunologic detection of certain antigenic products within LDL immune complexes, namely the modified LDL, such as ox-LDL and AGE-LDL.

Antibodies against modified LDL were prepared in the inventors' laboratory and are use to assess the level of these molecules in immune complexes in sample from a subject, such as serum or plasma. Both capture immunoassay and competitive immunoassay are useful in assessing LDL content of IC.

In one embodiment, antibodies to mod-LDL may be immobilized onto a selected surface, preferably a surface exhibiting a affinity for this molecule. After washing to remove incompletely adsorbed material, it is desirable to bind or coat the assay plate wells with a non-specific agent that is known to be antigenically neutral with regard to the test sample, e.g., bovine serum albumin (BSA), casein or solutions of powdered milk. This allows for blocking of non-specific adsorption sites on the immobilizing surface and thus reduces the background caused by non-specific binding of antibody to the surface. The surface then washed to remove unbound material, and the surface is then contacted with the sample to be tested in a manner conducive to specific binding of the antigen of interest.

Following formation of specific complexes between the immobilized antibodies and mod-LDL in the sample, and subsequent washing, the amount of antigen bound by the immobilized antibody may be determined by subjecting the same to a second antibody having specificity for the mod-LDL that is distinct from the first antibody. Appropriate conditions preferably include diluting the sample with diluents such as BSA, bovine gamma globulin (BGG) and phosphate buffered saline (PBS)/Tween®. These added agents also tend to assist in the reduction of non-specific background. The detecting antibody is then allowed to incubate for from about 2 to about 4 hr, at temperatures preferably on the order of about 21° to about 23° C. Following incubation, the surface is washed so as to remove unbound reagents. A preferred washing procedure includes washing with a solution such as PBS/Tween®, or borate buffer.

To provide a detecting means, the second antibody will preferably have an associated enzyme, such as a urease or peroxidase, that will generate a color development upon incubating with an appropriate chromogenic substrate. After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer. Other potential labels include isotopes, fluorescent labels, dyes and chemiluminescent molecules (e.g., luciferase).

Another format involves the use of the same primary antibody coated surface as above. However, rather than provide a secondary antibody for detection purposes, known amounts of labeled mod-LDL will be included in the mixture containing the target sample. By measuring the amount of bound labeled mod-LDL, one can determine the amount of unlabeled mod-LDL, i.e., the test level. Such an assay is termed a "competitive" immunoassay as the labeled (known) and unlabeled (test) mod-LDL compete with each other for antibody binding.

C. Other Mod-LDL Detection Methods i. Mass Spectrometry

By exploiting the intrinsic properties of mass and charge, mass spectrometry (MS) can resolve and confidently identify a wide variety of complex compounds, including nucleic acids and proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to the tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances, sample clean up is required (Nelson et al., 1994; Gobom et al., 2000).

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analyzed by the mass spectrometer in this method.

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode.

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff, 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Jiang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers such as proteins.

ii. Gas Chromatography

In the context of the present invention, it is useful to utilize gas chromatography to measure cholesterol to normalize the amount of LDL is a given quantity of a sample. Gas-liquid chromatograpy (GLC), or simply gas chromatography (GC), is a common type of chromatography used in analytic chemistry for separating and analyzing compounds that can be vaporized without decomposition. Gas chromatography is also sometimes known as vapor-phase chromatography (VPC), or gas-liquid partition chromatography (GLPC). Typical uses of GC include testing the purity of a particular substance, or separating the different components of a mixture (the relative amounts of such components can also be determined). In some situations, GC may help in identifying a compound. In preparative chromatography, GC can be used to prepare pure compounds from a mixture.

In gas chromatography, the moving or mobile phase is a carrier gas, usually an inert gas such as helium or an unreactive gas such as nitrogen. The stationary phase is a microscopic layer of liquid or polymer on an inert solid support, inside a piece of glass or metal tubing called a column (an homage to the fractionating column used in distillation). The instrument used to perform gas chromatography is called a gas chromatograph.

The gaseous compounds being analyzed interact with the walls of the column, which is coated with different stationary phases. This causes each compound to elute at a different time, known as the retention time of the compound. The comparison of retention times is what gives GC its analytical usefulness.

Gas chromatography is in principle similar to column chromatography (as well as other forms of chromatography, such as HPLC, TLC), but has several notable differences. Firstly, the process of separating the compounds in a mixture is carried out between a liquid stationary phase and a gas moving phase, whereas in column chromatography the stationary phase is a solid and the moving phase is a liquid. Hence, the full name of the procedure is "gas-liquid chromatography," referring to the mobile and stationary phases, respectively. Secondly, the column through which the gas phase passes is located in an oven where the temperature of the gas can be controlled, whereas column chromatography (typically) has no such temperature control. Thirdly, the concentration of a compound in the gas phase is solely a function of the vapor pressure of the gas.

Gas chromatography is also similar to fractional distillation, since both processes separate the components of a mixture primarily based on boiling point (or vapor pressure) differences. However, fractional distillation is typically used to separate components of a mixture on a large scale, whereas GC can be used on a much smaller scale (i.e. microscale).

In a GC analysis, a known volume of gaseous or liquid analyte is injected into the entrance (head) of the column, usually using a microsyringe (or, solid phase microextraction fibers, or a gas source switching system). As the carrier gas sweeps the analyte molecules through the column, this motion is inhibited by the adsorption of the analyte molecules either onto the column walls or onto packing materials in the column. The rate at which the molecules progress along the column depends on the strength of adsorption, which in turn depends on the type of molecule and on the stationary phase materials. Since each type of molecule has a different rate of progression, the various components of the analyte mixture are separated as they progress along the column and reach the end of the column at different times (retention time). A detector is used to monitor the outlet stream from the column; thus, the time at which each component reaches the outlet and the amount of that component can be determined. Generally, substances are identified (qualitatively) by the order in which they emerge (elute) from the column and by the retention time of the analyte in the column.

iii. Gel Electrophoresis

Gel electrophoresis is a technique used for the separation of deoxyribonucleic acid (DNA), ribonucleic acid (RNA), or protein molecules using an electric current applied to a gel matrix. DNA Gel electrophoresis is usually performed for analytical purposes, but may be used as a preparative technique prior to use of other methods such as mass spectrometry, RFLP, PCR, cloning, DNA sequencing, or Southern blotting for further characterization.

The term "gel" in this instance refers to the matrix used to contain, then separate the target molecules. In most cases, the gel is a crosslinked polymer whose composition and porosity is chosen based on the specific weight and composition of the target to be analyzed. When separating proteins or small nucleic acids (DNA, RNA, or oligonucleotides) the gel is usually composed of different concentrations of acrylamide and a cross-linker, producing different sized mesh networks of polyacrylamide. Agarose is composed of long unbranched chains of uncharged carbohydrate without cross links resulting in a gel with large pores allowing for the separation of macromolecules and macromolecular complexes.

"Electrophoresis" refers to the electromotive force (EMF) that is used to move the molecules through the gel matrix. By placing the molecules in wells in the gel and applying an electric current, the molecules will move through the matrix at different rates, determined largely by their mass when the charge to mass ratio (Z) of all species is uniform, toward the anode if negatively charged or toward the cathode if positively charged.

After the electrophoresis is complete, the molecules in the gel can be stained to make them visible. Ethidium bromide, silver, or coomassie blue dye may be used for this process. Other methods may also be used to visualize the separation of the mixture's components on the gel. If the analyte molecules fluoresce under ultraviolet light, a photograph can be taken of the gel under ultraviolet lighting conditions. If the molecules to be separated contain radioactivity added for visibility, an autoradiogram can be recorded of the gel.

If several mixtures have initially been injected next to each other, they will run parallel in individual lanes. Depending on the number of different molecules, each lane shows separation of the components from the original mixture as one or more distinct bands, one band per component. Incomplete separation of the components can lead to overlapping bands, or to indistinguishable smears representing multiple unresolved components.

Bands in different lanes that end up at the same distance from the top contain molecules that passed through the gel with the same speed, which usually means they are approximately the same size. There are molecular weight size markers available that contain a mixture of molecules of known sizes. If such a marker was run on one lane in the gel parallel to the unknown samples, the bands observed can be compared to those of the unknown in order to determine their size. The distance a band travels is approximately inversely proportional to the logarithm of the size of the molecule.

D. Mod-LDL Levels

As can be seen below in the Examples (Tables 1-9), the normal (lower quartile) levels for ox-LDL-IC are 5-89 mg/ml, for AGE-LDL-IC are 0.15-2.64 mg/ml, and for MDA-LDL-IC are 3-43 mg/ml. The concentrations of the modified LDL in these immune complexes are normalized per µg of LDL-Apolipoprotein B or per µg of LDL-cholesterol, and the total level of IC per ml of serum is calculated by multiplying the modified LDL levels by the total level of cholesterol or Apolipoprotein B in the IC precipitated from one ml of serum.

V. TREATMENTS

In other embodiments of the present invention, methods for treating CAD are provided, either alone or in conjunction with the methods set forth above to assess efficacy of the treatment. Also contemplated are combination therapies (see below).

A. Pharmaceutical Formulations

As used herein, by an "effective" amount or a "therapeutically effective amount" of a drug or active agent (e.g., an antibody or antifungal drug) is meant a non-toxic but sufficient amount of the drug or agent to provide the desired effect, i.e., reducing or eliminating fungal cell growth, differentiation, or dissemination. It is recognized that the effective amount of a drug or active agent will vary depending on the route of administration, the selected drug or active agent, and the species to which the drug or pharmacologically active agent is administered. It is also recognized that one of skill in the art will determine appropriate effective amounts by taking into account such factors as metabolism, bioavailability, and other factors that affect plasma levels of the drug or active agent. A drug or active agent may be administered by any route of administration sufficient to achieve the desired effect, including by aerosol or intravenous administration.

B. Coronary Artery Disease

Therapeutic options for coronary artery disease today are based on three principles: medical treatment—drugs (e.g., cholesterol lowering medications, beta-blockers, nitroglycerin, calcium antagonists, etc.); coronary interventions as angioplasty and coronary stent-implantation; and coronary artery bypass grafting (CABG—coronary artery bypass surgery). Recent research efforts focus on new angiogenic treatment modalities (angiogenesis) and various (adult) stem cell therapies.

Aspirin, in doses of less than 75 to 81 mg/d, can reduce the incidence of cardiovascular events. The U.S. Preventive Services Task Force 'strongly recommends that clinicians discuss aspirin chemoprevention with adults who are at increased risk for coronary artery disease.' The Task Force defines increased risk as men older than 40 years of age, postmenopausal women, and younger persons with risk factors for coronary artery disease (for example, hypertension, diabetes, or smoking) are at increased risk for heart disease and may wish to consider aspirin therapy. More specifically, high-risk persons are those with a 5-year risk≥3%.

C. Diabetes

The principal treatment of type 1 diabetes, even in its earliest stages, is the delivery of artificial insulin via injection combined with careful monitoring of blood glucose levels using blood testing monitors. Without insulin, diabetic ketoacidosis often develops which may result in coma or death. Treatment emphasis is now also placed on lifestyle adjustments (diet and exercise) though these cannot reverse the progress of the disease. Apart from the common subcutaneous injections, it is also possible to deliver insulin by a pump, which allows continuous infusion of insulin 24 hours a day at preset levels, and the ability to program doses (a bolus) of insulin as needed at meal times. An inhaled form of insulin was approved by the FDA in January 2006, although it was discontinued for business reasons in October 2007. Non-insulin treatments, such as monoclonal antibodies and stem-cell based therapies, are effective in animal models but have not yet completed clinical trials in humans.

Type 1 treatment must be continued indefinitely in essentially all cases. Treatment need not significantly impair normal activities, if sufficient patient training, awareness, appropriate care, discipline in testing and dosing of insulin is taken. However, treatment is burdensome for patients; insulin is replaced in a non-physiological manner, and this approach is therefore far from ideal. The average glucose level for the type 1 patient should be as close to normal (80-120 mg/dl, 4-6 mmol/L) as is safely possible. Some physicians suggest up to 140-150 mg/dl (7-7.5 mmol/L) for those having trouble with lower values, such as frequent hypoglycemic events. Values above 400 mg/dl (20 mmol/L) are sometimes accompanied by discomfort and frequent urination leading to dehydration. Values above 600 mg/dl (30 mmol/L) usually require medical treatment and may lead to ketoacidosis, although they are not immediately life-threatening. However, low levels of blood glucose, called hypoglycemia, may lead to seizures or episodes of unconsciousness and absolutely must be treated immediately, via emergency high-glucose gel placed in the patient's mouth, intravenous administration of dextrose, or an injection of glucagon.

D. Autoimmune/Inflammatory Disorders

Autoimmune diseases and inflammatory disorders are typically treated by anti-inflammatory agents, immunosuppressive agents, or combinations thereof.

Immunosuppressive agents include glucocorticoids, cytostatics, alkylating agents (cyclophosphamide, nitrosoureas, platinum compounds), antimetabolites (folic acid analogues, such as methotrexate, purine analogues such as azathioprine and mercaptopurine, pyrimidine analogues, protein synthesis inhibitors), cytotoxic antibiotics (dactinomycin, anthracyclines, mitomycin C, bleomycin, mithramycin), humanzied monoclonal antibodies (e.g., anti-CD20, anti-CD25, anti-CD3), T-cell receptor directed antibodies, cyclosporin, tacrolimus, sirolimus (rapamycin, trade name Rapamune), interferons, opioids, TNF binding proteins, mycophenolate and small biological agents (Fingolimod, Myriocin).

Anti-inflammatory agents include steroids, specifically glucocorticoids, non-steroidal anti-inflammatory drugs (NSAIDs), including aspirin, ibuprofen, and naproxen.

E. Combination Therapies

In order improve the performance of a given therapy, one may combine distinct therapeutic modalities with hope of providing additive, and possibly synergistic affects, or to achieve an effective therapy a doses lower than that required for either agent alone. This process may involve administering both agents at the same time. This may be achieved by administering a single composition or pharmacological formulation that includes both agents, or by administering two distinct compositions or formulations at the same time.

Alternatively, one agent may precede or follow the other agent treatment by intervals ranging from minutes to weeks. In embodiments where the other agents are applied separately, one would generally ensure that a significant period of time did not expire between the time of each delivery, such that the agents would still be able to exert an advantageously combined effect. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the antibody or the other agent will be desired. Various combinations may be employed, where the first agent is "A" and the second agent is "B," as exemplified below:

| |
|---|
| A/B/A B/A/B B/B/A A/A/B B/A/A A/B/B B/B/B/A B/B/A/B |
| A/A/B/B A/B/A/B A/B/B/A B/B/A/A B/A/B/A B/A/A/B B/B/B/A |
| A/A/A/B B/A/A/A A/B/A/A A/A/B/A A/B/B/B B/A/B/B B/B/A/B |

Other combinations are contemplated.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Subjects.

This study was performed on a subgroup of 479 subjects from the DCCT/EDIC cohort. The DCCT cohort included 1,441 patients who were 13-39 years of age and had Type 1 diabetes for 1-15 years at study entry (The Diabetes Control and Complications Trial Res. Group, 1993). None of the patients at entry into the study (1983-89) had hypertension or dyslipidemia and therefore were not on lipid-lowering or anti-hypertensive therapy.

The DCCT cohort was randomly assigned to intensive or conventional diabetes therapy and followed for an average of 6.5 years. In 1994, after intensive therapy had been demonstrated to have major beneficial effects on microvascular complications, the interventional phase of the study was stopped and the observational phase was initiated (Epidemiology of Diabetes Interventions and Complications (EDIC), 1999). During the ongoing EDIC observational phase, the patients have been under the care of their personal physicians and encouraged to practice intensive diabetes therapy.

Of the 1441 DCCT participants, 90-95% were followed during EDIC and 905 of these individuals had blood collected longitudinally as part of a sub-study. From these 905 subjects, 518 patients were selected for a case-control study of LDL-IC and albuminuria. Patients with at least 2 measurements of AER above 60 mg/24 hrs were selected as cases and 3-4 patients without albuminuria per patient with albuminuria were selected as controls. Of the 518 with LDL-IC measured 479 had IMT measured during EDIC (Hodis et al., 1998).

Serum samples were obtained after an overnight fast at entry into the DCCT study and assayed at the time or stored at −80° C. The DCCT and EDIC were approved by the Institutional Review Board of all participating DCCT/EDIC centers and all participants provided written informed consent.

Assessment of Carotid Intima-Media Thickness.

Carotid ultrasonography was first performed 1-2 years after initiation of EDIC (5-13 years after DCCT baseline) and repeated 5 years later. The measurement of IMT in the DCCT/EDIC cohort has been described in detail (Nathan et al., 2003; (Epidemiology of Diabetes Interventions and Complications (EDIC) Research Group, 1999). In brief, a single longitudinal lateral view of the distal 10 mm of the right and left common carotid arteries (CCA) and three longitudinal views in different imaging planes of each internal carotid artery (ICA) were obtained by certified technicians at the clinical centers, recorded on S-VHS tapes and read in a central unit (Tufts Medical Center, Boston, Mass.) by a single reader, masked to participant characteristics. The maximum IMT (mm) of the CCA was defined as the mean of the maximum IMT for near and far walls on both right and left sides. The maximum IMT of the ICA was defined in the same way, and the results of the three scans (i.e., anterior, lateral and posterior views of both sides) were averaged.

Measurement of AGE-LDL, oxLDL and MDA-LDL in Human Circulating Immune Complexes.

The inventors measured oxLDL, MDA-LDL and AGE-LDL by first precipitating circulating immune complexes from serum and then fractionating these IC by protein G affinity chromatography, separating the predominant IgG antibody from modified LDL, as previously described (Virella et al., 2008; Lopez-Virella et al., 2007). The reactivity of modified LDL separated from LDL-IC with antibodies specific for different LDL modifications (oxLDL, MDA-LDL and AGE-LDL) was then assayed with capture assays developed in the inventors' laboratory (Virella et al., 2005). The characteristics of the antibodies used in the assay and the specificity and reproducibility of the capture assays have been previously reported (Virella et al., 2004; Virella et al., 2005). Coefficients of variation for 50 samples measured in two separate assays were 5.2% for oxLDL, 0.5% for MDA-LDL, and 8.3% for AGE-LDL. The development of standards for calibration of the oxLDL, MDA-LDL, and AGE-LDL assays, as well as sensitivity, reproducibility, and recovery data for the capture assays have been reported elsewhere (Virella et al., 2005). The levels of the different LDL modifications in human circulating IC were expressed in function of the amount of apolipoprotein B contained in the IC and the final values given as the concentration per mL of serum.

Other Procedures.

At baseline DCCT, each participant completed a standardized medical history, physical examination, electrocardiogram and laboratory testing including hemoglobin A1c (Epidemiology of Diabetes Interventions and Complications (EDIC), 1999; The Diabetes care and Complications Trial (DCCT) Research Group, 1987), fasting lipid profiles and 4-hour urine collections for measurement of AER and creatinine clearance. Covariates for the current analyses were obtained from DCCT baseline history, physical examination and laboratory data (fasting lipids and renal function). The methodologies to measure conventional CVD risk factors have been described elsewhere (Epidemiology of Diabetes Interventions and Complications (EDIC), 1999; The Diabetes care and Complications Trial (DCCT) Research Group, 1987). Retinopathy status at baseline was assessed with stereo fundus photography (Early Treatment Diabetic Retinopathy Study Res. Group, 1991).

Statistical Analysis.

Prospective analyses were carried out in which the levels of oxLDL, AGE-LDL and MDA-LDL in LDL-IC, measured at baseline DCCT, functioned as a biomarker for individual's levels of LDL, degree of oxidative stress and immune response and internal and common IMT levels 8-14 years later (EDIC years 1 and 6) were the outcomes of interest. All modified LDL values were standardized to mg of Apolipoprotein-B per L of serum and are expressed as mg/L; in addition, modified LDL values were log transformed due to their skewed, non-normal distribution. Spearman correlations were determined for modified LDL levels and baseline DCCT variables of interest. Means and proportions adjusted for treatment group, retinopathy status, age and sex were determined for participant DCCT baseline characteristics stratified by modified LDL quartile using linear and logistic regression as appropriate. Linear regression was used to determine estimates of the β coefficient and semi-partial $R^2$ for the relationship between the level of each type of modified LDL measured in LDL-IC and internal and common IMT (ICA and CCA IMT) measurements at EDIC years 1 and 6 and to calculate least square means for EDIC year 1 and 6 ICA/CCA IMT across quartiles of each modified LDL. Trends in both internal and common IMT across quartiles of each modified LDL were tested using a F-statistic obtained from a generalized linear model adjusted for treatment group, retinopathy cohort, age, sex, diabetes duration, hemoglobin A1c, logarithm of AER and ultrasonography equipment.

Logistic regression was used to model the odds ratio associated with being in the upper versus lower measurements of ICA IMT (i.e., high versus normal) at EDIC year 6. For logistic regression analysis each IC was categorized into quartiles. The association between modified LDL quartiles and being in the upper quintile of ICA IMT was assessed separately for modified LDL after controlling for the covariates included in the linear regression models with the addition of LDL and HDL-cholesterol, systolic and diastolic blood pressure and current smoking status. Additionally, for each IC studied appropriate interaction terms were used to determine whether covariates modified the relationship between each type of modified LDL and having high ICA IMT at EDIC Year 6. Finally, the c-statistic or area under the receiver-operating curve (ROC AUC) was used to compare the discriminatory power of various multivariate models. Reported p-values are two-sided with a type-I error rate for significance of α=0.05. All analysis were performed using SAS v. 9.2 (SAS Institute, Cary, N.C., USA).

Example 2

Results

At DCCT baseline, the mean age of the study population was 27.1±7.0 years, the mean duration of diabetes was 6.0±4.2 years, 247 (51.6%) of the 479 subjects studied were males and 45.7% were assigned to the DCCT intensive treatment group. Comparing DCCT baseline characteristics of the 479 subjects with the remaining DCCT cohort show that duration of diabetes was longer, they were more likely to have retinopathy at baseline and body mass index and AER were higher. Blood pressure, lipid, and hemoglobin A1c as well as age, gender, drinking and smoking status were similar in those included and excluded in this study's subcohort.

At DCCT baseline, the levels of oxLDL, AGE-LDL and MDA-LDL in isolated LDL-IC were significantly correlated with diabetes duration, BMI, lipid and blood pressure levels, but not with age. Correlations with LDL-cholesterol while statistically significant were of moderate magnitude (r=0.15 to 0.23, p<0.0007 to p<0.0001). The levels of MDA-LDL, AGE-LDL and oxLDL in LDL-IC were all highly inter-correlated (r=0.71 to 0.83, p<0.0001).

The percentage of men increased with increasing quartiles of oxLDL in LDL-IC (Table 1). After adjusting for treatment group, retinopathy status, age and gender, the duration of diabetes remained similar while BMI, hemoglobin A1c, LDL-cholesterol and triglyceride levels increased across quartiles of oxLDL in LDL-IC. HDL-cholesterol levels decreased across increasing quartiles of oxLDL in LDL-IC. Systolic blood pressure, diastolic blood pressure, AER and creatinine clearance did not increase or decrease across increasing oxLDL quartiles. Finally, neither current smoking status nor alcohol consumption appeared to be associated with oxLDL quartiles.

Figure 1:
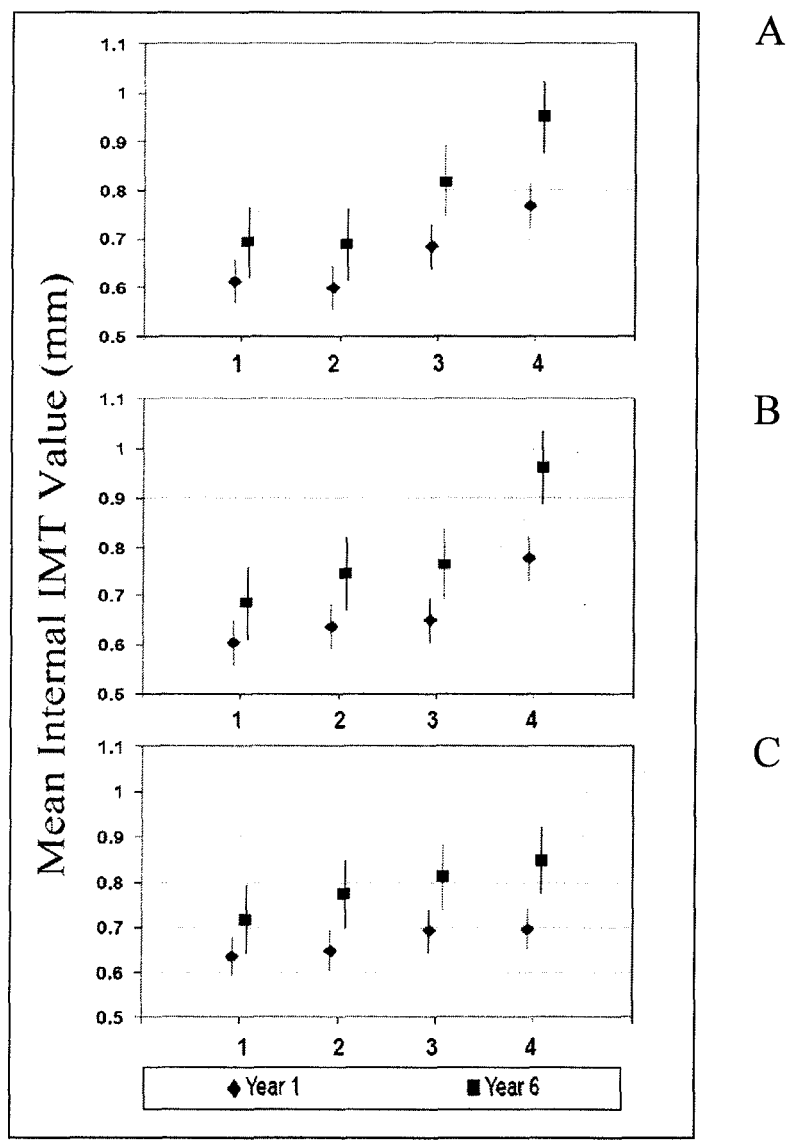
FIGS. 1A-C. Internal IMT means (mm) for years 1 and 6 adjusted for age, gender, study group, retinopathy status, duration of diabetes at study entry, hemoglobin A1c %, logarithm of AER and ultrasonography equipment.

After adjusting for covariates, the concentrations of modified LDL in isolated IC were each significantly associated with EDIC year 1 and EDIC year 6 ICA IMT with higher modified LDL levels predicting higher internal carotid artery IMT (Table 2). For common carotid artery IMT, associations were slightly weaker with log MDA-LDL failing to predict higher CCA IMT at EDIC year 1 or EDIC year 6. Focusing on mean internal carotid artery IMT levels as the outcome and stratifying by oxLDL quartiles, ICA IMT levels increased across oxLDL quartiles at EDIC year 1 (Linear Trend Test; P<0.001) and EDIC year 6 (Linear Trend Test; P<0.001) after adjusting for treatment group, retinopathy cohort, age, sex, diabetes duration, hemoglobin A1c, logarithm of AER and ultrasonography equipment (FIG. 1A). Similar findings were observed across AGE-LDL quartiles (FIG. 1B), while slightly weaker but still statistically significant findings were observed across and MDA-LDL quartiles (FIG. 1C).

Multivariate logistic regression models were used to further examine the ability of the concentrations of oxLDL and AGE-LDL in isolated LDL-IC to predict internal carotid artery IMT (Table 3). The outcome, high internal carotid artery IMT, was defined as being in the upper quintile as compared to the lower 4 quintiles of ICA IMT at EDIC year 6 (high IMT defined as >0.845 mm). Individuals in the highest quartile of oxLDL in isolated LDL-IC had a 7-fold increased odds [7.72 (95% CI: 3.27, 18.3)] of having high versus normal internal carotid artery IMT relative to those in the lowest quartile of oxLDL, after controlling for treatment group, retinopathy cohort, age, sex, diabetes duration, hemoglobin A1c, logarithm of AER and ultrasonography equipment. Additionally adjusting for LDL-cholesterol, HDL-cholesterol, diastolic blood pressure and smoking status attenuated the odds ratios somewhat to 6.11 (95% CI: 2.51, 14.8). Parallel analyses for AGE-LDL resulted in odds ratios of 7.82 (95% CI: 3.17, 19.3) and 6.40 (95% CI: 2.53, 16.2), respectively. Parallel analyses for MDA-LDL, not shown in Table 3, resulted in odds ratios of 2.74 (95% CI: 1.27, 5.92) and 2.39 (95% CI: 1.06, 5.38), respectively. None of the covariates examined were found to modify associations between oxLDL or AGE-LDL levels in isolated LDL-IC and having high internal carotid artery IMT at EDIC year 6.

Figure 2:
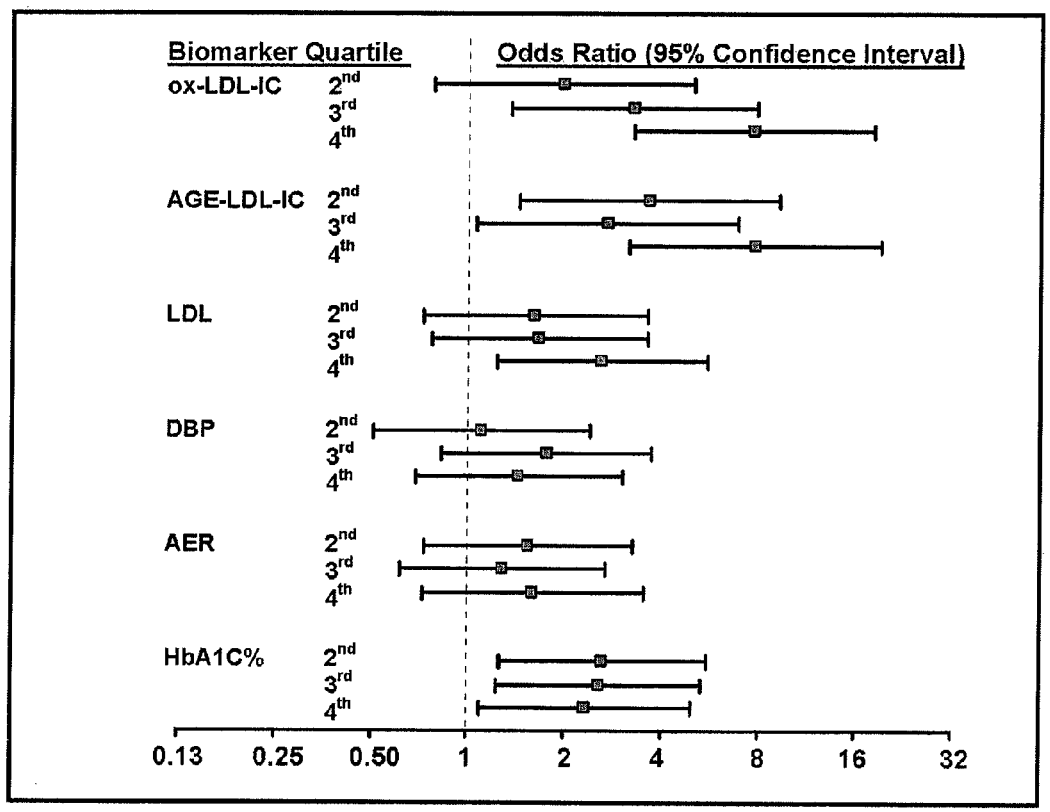
FIG. 2. Adjusted* odds ratios with 95% confidence intervals (calculated from multivariate logistic regression models) for given levels of oxLDL in isolated LDL-IC, AGE-LDL in isolated LDL-IC, LDL cholesterol, diastolic blood pressure (DBP), albumin excretion rate (AER) and hemoglobin A1c (levels in the $2^{nd}$, $3^{rd}$ and $4^{th}$ quartiles relative to quartile 1) to predict internal carotid artery intima-media thickness at EDIC year 6. OxLDL-IC categories are 5-89, 90-162, 163-305 and 306-1382 mg/L; AGE-LDL-IC categories are 0.15-2.64, 2.65-6.42, 6.43-12.03, 12.17-305.34 mg/L; LDL categories are 29-89, 90-105, 106-126 and 127-219 mg/dL; DBP categories are 40-66, 68-73, 74-79 and 80-98 mm Hg; AER categories are 1.4-6.0, 7.0-10, 11-19 and 20-151 mg/24 hr; hemoglobin A1C categories are 5.9-7.7, 7.7-8.5, 8.5-9.9 and 9.9-14.4%. High carotid artery IMT was defined as being in the upper quintile as compared to the lower 4 quintiles of Internal carotid artery IMT at EDIC year 6. The numerical cut-point for high IMT at EDIC year 6 was greater than 0.845 mm. *Adjusted for age, gender, study group, retinopathy status, duration of diabetes at study entry, logarithm of AER (except for when AER is the categorical variable), hemoglobin A1c % (except for when hemoglobin A1c is the categorical variable), and ultrasonography equipment.

Finally, comparing the discriminatory power of oxLDL and AGE-LDL concentrations in isolated LDL-IC to that of LDL-cholesterol, diastolic blood pressure, AER and hemoglobin A1c, the adjusted odds ratios for having high versus normal internal carotid artery IMT, comparing those in the highest versus lowest quartile of LDL-cholesterol, diastolic blood pressure, AER and hemoglobin A1c were 2.62 (95% CI: 1.24, 5.55), 1.45 (95% CI: 0.69, 3.03), 1.61 (95% CI: 0.73, 3.56), and 2.33 (95% CI: 1.09, 4.99), respectively (FIG. 2). Furthermore, the areas under the receiver-operating curve (ROC AUC), used as mentioned in methods to compare the discriminatory power of the various multivariate models, were 0.750, 0.740, 0.739, respectively for LDL-cholesterol, diastolic blood pressure and AER models, and 0.747 for the hemoglobin A1c model. In comparison, the ROC AUC for the analogous models for oxLDL and AGE-LDL in LDL-IC were 0.794 and 0.790, respectively.

Example 3

Discussion

This study has shown that high levels of oxLDL and AGE-LDL in circulating IC, even when measured at a very young age and when the patient is completely free of macrovascular disease, are strongly predictive of increased intima-media thickening over a period of 8-14 years. The associations of the modified lipoprotein levels in circulating IC with internal carotid artery IMT were generally larger than those of classical predictive factors such as albumin excretion rate, LDL-cholesterol, hemoglobin A1c or blood pressure.

The inter-correlation between the levels of MDA-LDL, AGE-LDL and oxLDL in circulating IC was to be expected, since the precipitated IC are not necessarily made of LDL molecules with single modifications, but rather of LDL molecules with multiple epitopes formed by different mechanisms, recognized by antibodies of different specificities. Furthermore, some of the epitopes, such as CML, are shared by AGE-LDL and oxLDL (Virella et al., 2004). Therefore, the inventors' measurements reflect the relative distribution of epitopes related to copper oxidation, MDA and AGE modifications in the population of modified LDL molecules involved in IC formation. Interestingly, the levels of MDA-LDL were not as predictive of internal carotid artery IMT. The inventors have shown that copper-oxidized LDL contains non-MDA epitopes recognized by human antibodies (Virella et al., 2004). This observation suggests that although MDA epitopes are present in modified LDL from isolated IC, the antibodies involved in IC formation react predominantly with non-MDA epitopes and this could explain why the measurement of oxLDL in isolated LDL-IC is a better predictor of CVD.

The pro-inflammatory properties of LDL immune complexes have been well characterized (Virella and Tsokos, 2007). Their pathogenic potential result from the fact that human modified LDL antibodies are predominantly of the IgG isotype, which can diffuse easily across the endothelial barrier. In addition, modified LDL antibodies are predominantly of the IgG1 and IgG3 isotypes (Virella and Lopes-Virella, 2003; Virella et al., 2008; Virella et al., 2000; Virella et al., 2003), able to activate the complement system by the classical pathway (Michalesen et al., 2009) and to interact with Fcg receptors in phagocytic cells (Burton and Woof, 1992), specifically macrophages in the vessel wall, and therefore promote cell activation and inflammation. Given that both circulating and complexed human autoantibodies to both oxLDL and AGE-LDL are predominantly IgG of the IgG1 an IgG3 isotypes (Virella and Lopes-Virella, 2003; Virella et al., 2008; Saad et al, 2006; Virella et al., 2000; Virella et al., 2003), it would be fully expected that they could play a pathogenic role in chronic inflammatory processes, such as atherosclerosis.

A limitation of this study is that the measurement of modified lipoproteins in IC isolated from peripheral blood is only a surrogate marker for the formation of extravascular IC; however, it is very likely that these peripheral IC levels are reasonable surrogate markers since both modified LDL and the corresponding antibodies have been identified in atheromatous lesions (Yla-Herttuala et al., 1980; Yla-Herttuala et al., 1994). A second limitation of the study is that the 479 participants with IC measurements available, because selected for a case-control study of albuminuria, were not a random sample of the entire DCCT/EDIC study population. To overcome this selection bias, the inventors have controlled for DCCT retinopathy cohort, AER, diabetes duration, and hemoglobin A1C and the inventors determined that covariates including DCCT treatment group were not acting as effect modifiers of associations of interest indicating that the predictive ability of modified LDL-IC was similar across different levels of these variables.

The measurement of LDL modifications in isolated IC reflects three important steps in the development of the arteriosclerotic process: increased levels of LDL cholesterol, clearly associated with the development of atherosclerosis; increased oxidation and glycoxidative modification of LDL in diabetes; and the impact of the humoral immune response in the inflammatory process associated with atherosclerosis.

While AGE-LDL modification is more accentuated in hyperglycemic patients, LDL oxidation seems to be a universal event, affecting the general population. Also, the same predominance of IgG1 and IgG3 oxLDL antibodies has been found in non-diabetic patients and healthy controls (Mironova et al., 1996). Therefore, the pathogenic role of modified LDL in circulating IC should not be limited to diabetic patients. However it is possible that patients with type 1 diabetes not only generate higher levels of modified LDL through glyco-oxidative processes, but given the complex constellation of genetic factors associated with their autoimmune disease they could have an enhanced and more potent autoimmune response to modified lipoproteins. It is therefore quite important to investigate whether the same high predictive value of modified LDL in circulating IC for CVD events is also present in type 2 diabetes and in the general population.

Regardless of the results of such studies, it is however quite clear that high levels of oxLDL and AGE-LDL in circulating IC have a major impact on the progression of carotid IMT in type 1 diabetes and they help to identify patients at high risk for CVD events when the other conventional CVD risk factors are still within or close to normal levels.

TABLE 1

DCCT Baseline characteristics (means or proportions and 95% confidence intervals) of the study population stratified by quartile of oxLDL in LDL-IC (n = 479) adjusted for treatment group, retinopathy cohort, age and sex.

| | oxLDL in LDL-IC Quartiles (cut-points, mg/L) | | | | Trend |
|---|---|---|---|---|---|
| | $1^{st}$ (5-89) | $2^{nd}$ (90-162) | $3^{rd}$ (163-305) | $4^{th}$ (306-1382) | P |
| Age* (years) | 27.0 (25.7 28.2) | 27.1 (25.9 28.4) | 27.3 (26.0 28.5) | 27.1 (25.9 28.4) | 0.8235 |
| Male* (%) | 42.0 (33.5, 51.0) | 47.5 (38.7, 56.4) | 59.2 (50.2, 67.6) | 57.5 (48.5, 66.0) | 0.0047 |
| Intensive Treatment Group* (%) | 52.1 (43.2, 60.9) | 48.3 (39.5, 57.2) | 46.7 (37.9, 55.6) | 35.8 (27.8, 44.8) | 0.0135 |
| Primary Retinopathy Cohort* (%) | 54.6 (45.6, 63.3) | 44.2 (35.6, 53.1) | 51.7 (42.8, 60.5) | 70.8 (62.1, 78.3) | 0.0058 |
| Diabetes Duration (years) | 5.5 (5.0 6.0) | 6.5 (6.0 7.0) | 6.1 (5.6 6.6) | 5.9 (5.4 6.4) | 0.4827 |
| Hemoglobin A1c (%) | 8.7 (8.4 9.0) | 8.6 (8.3 8.8) | 8.9 (8.6 9.2) | 9.3 (9.0 9.6) | 0.0014 |
| Body Mass Index (kg/m$^2$) | 23.1 (22.6 23.6) | 23.3 (22.8 23.8) | 23.4 (22.9 23.9) | 24.1 (23.6 24.6) | 0.0062 |
| Systolic Blood Pressure (mmHg) | 113 (111 115) | 115 (113 117) | 115 (113 117) | 115 (113 117) | 0.2216 |
| Diastolic Blood Pressure (mmHg) | 73 (71 74) | 73 (71 74) | 73 (71 74) | 74 (73 76) | 0.2266 |
| HDL-Cholesterol (mg/dl) | 53 (51 55) | 51 (49 53) | 50 (48 52) | 49 (47 51) | 0.0058 |
| LDL-Cholesterol (mg/dl) | 103 (98 108) | 102 (97 108) | 113 (108 118) | 118 (113 123) | <0.0001 |
| Triglycerides† (mg/dl) | 66 (62 71) | 68 (63 73) | 76 (70 81) | 82 (77 88) | <0.0001 |
| AER† (mg/24 hr) | 10.7 (9.4 12.3) | 11.6 (10.2 13.3) | 12.5 (10.9 14.3) | 12.6 (11.0 14.4) | 0.0754 |
| Creatinine Clearance (ml/min) | 125 (120 129) | 126 (121 131) | 131 (126 136) | 125 (121 130) | 0.4882 |
| Current Smoker (%) | 13.5 (8.4, 20.9) | 25.6 (18.4, 34.4) | 17.0 (11.3, 24.8) | 23.3 (16.3, 32.2) | 0.2083 |
| Current Drinker (%) | 26.9 (19.3, 36.0) | 14.0 (8.8, 21.5) | 16.7 (11.1, 24.5) | 16.5 (10.8, 24.3) | 0.0961 |

AER, albumin excretion rate;

*Unadjusted;

†Due to non-normal distributions geometric means are presented.

TABLE 2

Summary of linear regression models for modified LDL in LDL-IC predicting internal and common carotid IMT adjusted for DCCT treatment group, DCCT retinopathy cohort and baseline DCCT age, sex, diabetes duration, hemoglobinA1C (%), logarithm of AER and ultrasonography equipment.

| | β Coefficient Estimate | P | Semipartial $R^2$ (%) | β Coefficient Estimate | P | Semipartial $R^2$ (%) |
|---|---|---|---|---|---|---|
| | Internal IMT (mm) - year 1 | | | Internal IMT (mm) - year 6 | | |
| Ln oxLDL in IC* | 0.05965 | <.0001 | 4.28 | 0.11000 | <.0001 | 5.52 |
| Ln AGE-LDL in IC* | 0.04684 | <.0001 | 4.25 | 0.08942 | <.0001 | 5.89 |
| Ln MDA-LDL in IC* | 0.02369 | 0.0306 | 1.03 | 0.04208 | 0.0172 | 1.24 |
| | Common IMT (mm) - year 10 | | | Common IMT (mm) - year 6 | | |
| Ln oxLDL in IC* | 0.00855 | 0.0460 | 0.85 | 0.01908 | 0.0035 | 1.82 |
| Ln AGE-LDL in IC* | 0.00645 | 0.0562 | 0.78 | 0.01475 | 0.0043 | 1.76 |
| Ln MDA-LDL in IC* | 0.00282 | 0.4181 | 0.14 | 0.00781 | 0.1420 | 0.47 |

*β Coefficient Estimates are per unit increase in natural log transformed levels of modified LDL forms in isolated LDL-IC (mg/L).

TABLE 3

Adjusted* odds ratios (and 95% confidence intervals) from multivariate logistic regression models for a given difference in risk factor level for being in the upper quintile versus the lower four quintiles† of internal carotid artery intima-media thickness at EDIC year 6.

| | ox-LDL in LDL-IC | | AGE-LDL in LDL-IC | |
|---|---|---|---|---|
| Immune Complex | Model 1 | Model 2 | Model 3 | Model 4 |
| Lowest Quartile | 1.00 | 1.00 | 1.00 | 1.00 |
| Quartile 2 | 1.98 (0.78, 5.02) | 1.77 (0.68, 4.60) | 3.65 (1.44, 9.26) | 3.66 (1.40, 9.56) |
| Quartile 3 | 3.27 (1.35, 7.91) | 2.88 (1.16, 7.15) | 2.71 (1.06, 6.93) | 2.75 (1.05, 7.21) |
| Quartile 4 | 7.72 (3.27, 18.3) | 6.11 (2.51, 14.8) | 7.82 (3.17, 19.3) | 6.40 (2.53, 16.2) |
| Age (1 year increase) | 1.12 (1.08, 1.17) | 1.10 (1.06, 1.15) | 1.12 (1.07, 1.16) | 1.10 (1.05, 1.15) |
| Gender (men vs. women) | 1.97 (1.16, 3.35) | 1.27 (0.69, 2.33) | 2.10 (1.24, 3.57) | 1.30 (0.71, 2.38) |
| Study Group (Intensive vs. Conventional) | 0.72 (0.42, 1.22) | 0.67 (0.39, 1.16) | 0.68 (0.40, 1.15) | 0.64 (0.37, 1.11) |
| Retinopathy Cohort (Second vs. Primary) | 0.58 (0.26, 1.28) | 0.51 (0.22, 1.18) | 0.69 (0.32, 1.48) | 0.60 (0.27, 1.35) |
| Duration (1 year increase) | 1.07 (0.98, 1.17) | 1.08 (0.98, 1.18) | 1.09 (0.99, 1.19) | 1.09 (1.00, 1.20) |
| Hemoglobin A1c (1 unit increase, %) | 1.08 (0.91, 1.28) | 1.06 (0.89, 1.26) | 1.11 (0.94, 1.31) | 1.08 (0.91, 1.29) |
| Ln of AER (1 unit increase, mg/24 hr) | 1.14 (0.78, 1.66) | 0.95 (0.64, 1.41) | 1.11 (0.77, 1.62) | 0.93 (0.62, 1.37) |
| LDL-C (10 unit increase, mg/dL) | — | 1.10 (1.00, 1.21) | — | 1.11 (1.02, 1.22) |
| HDL-C (10 unit increase, mg/dL) | — | 0.69 (0.53, 0.91) | — | 0.67 (0.51, 0.88) |
| Diastolic BP‡ (10 unit increase, mmHg) | — | 1.39 (0.99, 1.95) | — | 1.52 (1.07, 2.15) |
| Current smoking (yes vs. no) | — | 2.31 (1.25, 4.26) | — | 2.23 (1.19, 4.15) |
| ROC AUC | 0.794 | 0.818 | 0.790 | 0.817 |

*All models are additionally adjusted for ultrasonography equipment.
†The numerical cut-point for high IMT at EDIC year 6 was greater than 0.845 mm.
‡Diastolic rather than systolic blood pressure was included because although not significantly associated with high internal carotid artery intima-media thickness, it was a stronger predictor than systolic blood pressure in the study population.

Example 4

Materials and Methods

Patients.

The Diabetes Control and Complications Trial (DCCT) was a randomized controlled trial of 1,441 patients who were 13-39 years of age and had Type 1 diabetes for 1-15 years at study entry (The Diabetes Control and Complications Trial Tes. Group, 1993). The participants were randomized to intensive or conventional insulin therapy and followed for an average of 6.5 years before the study was stopped early for efficacy by the study's Data and Safety Monitoring Board in 1993. In 1994, approximately 95% of the DCCT participants enrolled into the Epidemiology of Diabetes Interventions and Complications (EDIC) study. EDIC was initiated (Epidemiology of Diabetes Interventions and Complications (EDIC), 1999) to assess the development of macrovascular disease in Type 1 diabetes. During the EDIC observational phase, all patients were under the care of their personal physicians and encouraged to practice intensive insulin therapy; however, each EDIC participant underwent a standardized annual history, physical examination, resting ECG, and routine laboratory analysis that included $HbA_1c$ levels (Epidemiology of Diabetes Interventions and Complications (EDIC), 1999; The Diabetes Care and Complications Trial (DCCT) Research Group, 1987). Lipid profiles and 4-hour urine collections to measure albumin excretion rates (AER) were obtained in alternate years (Epidemiology of Diabetes Interventions and Complications (EDIC), 1999; The Diabetes Care and Complications Trial (DCCT) Research Group, 1987).

Figure 3:
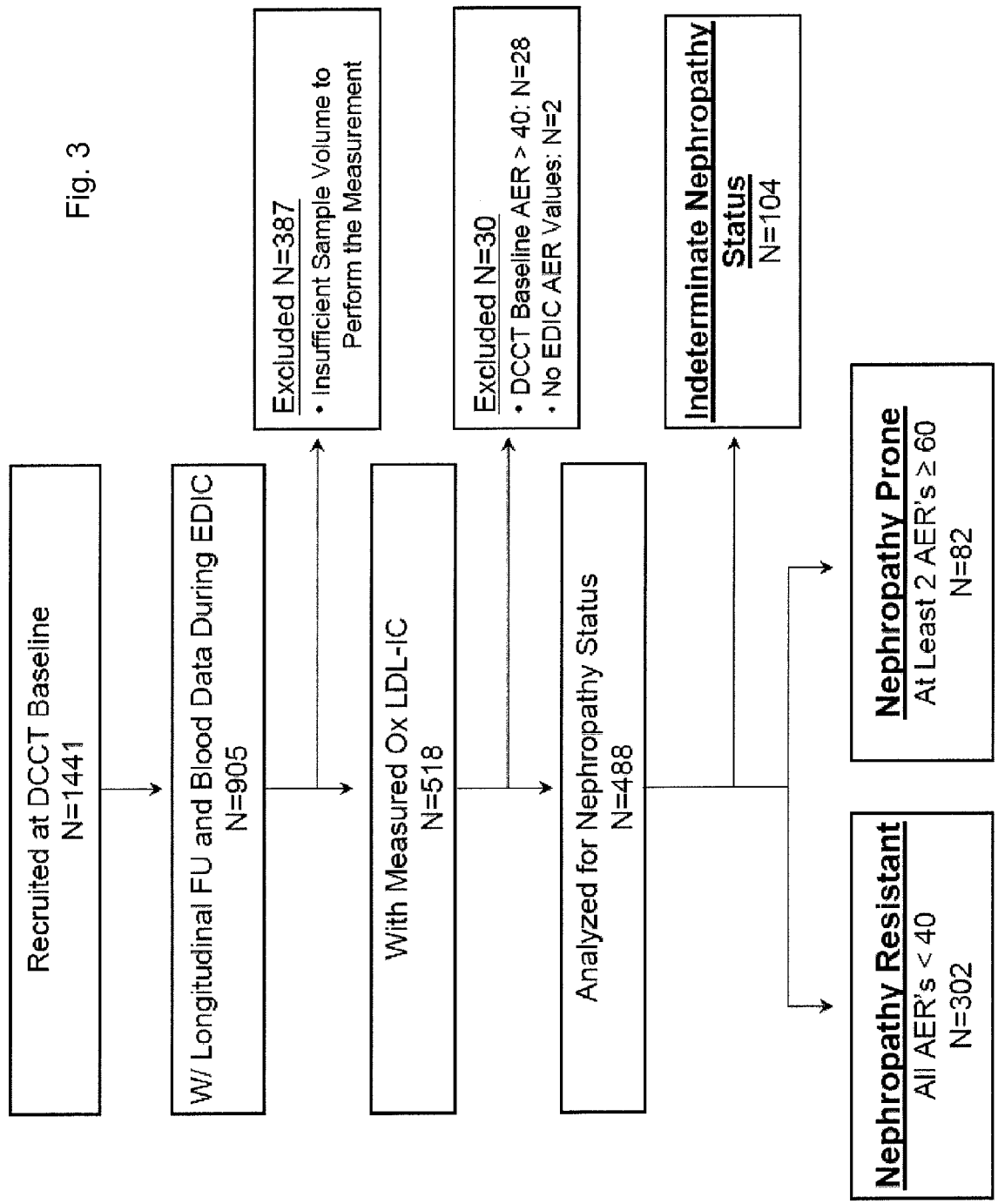
FIG. 3. Recruitment Flow Chart. 1441 subjects were recruited into the study at DCCT baseline. 905 of the subjects had longitudinal follow up and blood collection for the project during the EDIC phase. A total of 518 of those subjects had sufficient sample (≥800 mL of serum) to perform the Oxidized LDL-Immune complex measurements. Of those 518 subjects, 28 had elevated AER at baseline (>40 mg) and were excluded from the analysis. Additionally, 2 more subjects were removed due to a lack of EDIC AER data. The remaining 488 were then assessed for nephropathy status. 302 subjects had no AER values greater than 40 mg for the duration of DCCT and EDIC and were considered resistant to the development of nephropathy. 82 subjects had at least two AER measurements greater than or equal to 60 mg and were considered prone to the development of nephropathy. The remaining 104 subjects had at least one AER measurement over 40 mg but no more than one AER measurement over 60 mg. These subjects were not considered as either prone or resistant to develop nephropathy since they had a single measurement above 60 mg during the longitudinal follow-up. This abnormal AER measurement could however have been secondary to an asymptomatic urinary tract infection or to a urine collection performed after intensive physical exercise and therefore qualification of the patient into the resistant or prone group could not be properly made.

This study was performed on a subgroup of DCCT/EDIC participants to test the hypothesis that DCCT baseline values of modified LDL-IC would be associated with subsequent development of albuminuria. To be included in this study, participants needed normal (<40 mg/24 hr) albumin excretion rate (AER) at DCCT baseline and stored specimens with sufficient volume for analysis (FIG. 3). Those patients who developed albuminuria during DCCT and up to EDIC Year 9 were defined as nephropathy prone. Development of albuminuria was defined as at least two AERs >60 mg/24 hr. Participants with normal AER (<40 mg/24 h) throughout DCCT and up to EDIC year 9 were determined nephropathy resistant. DCCT/EDICT participants with AER>40 at DCCT baseline or with one single AER measurement over 60 mg/24 hr were excluded from the sampling frame (denoted as indeterminate nephropathy status in FIG. 3). A total of 384 patients, 82 (21%) of them considered nephropathy prone, met sampling criteria and were included in this analysis.

Samples.

Fasting serum samples obtained during DCCT/EDIC were sent to the DCCT/EDIC central laboratory for standard lipid analysis. Aliquots of these samples were archived for future research purposes. In 1999-2000, serum samples collected during DCCT were sent to Medical University of South Carolina by the DCCT/EDIC Coordinating Center and NIDDK to complement the serum sample collected during EDIC as part of a Medical University of SC Program Project Grant funded by the NIH/JDF. Since sample collection, the serum samples collected have been stored at −70° C. and refreezing effects have been minimized by preparing aliquots of the serum when thawed for the first time and using a new frozen aliquot for each new test performed. The Institutional Review Boards at Medical University of South Carolina and all participating DCCT/EDIC centers approved the sample collection procedures. Written informed consent was obtained from all participants.

Measurement of oxLDL and AGE-LDL Immune Complexes.

The inventors measured the content of oxLDL and AGE-LDL in circulating IC by first precipitating the IC from serum and then fractionating these IC by protein G affinity chromatography, separating the predominant IgG antibody from modified LDL, as previously described (Lopes-Virella et al., 2007; Virella et al., 2008). The reactivity of modified LDL separated from LDL-IC with antibodies specific for different LDL modifications (oxLDL and AGE-LDL) was then assayed with capture assays developed in the inventors' laboratory (Virella et al., 2005). The characteristics of the antibodies used in the assay and the specificity and reproducibility of the capture assays have been previously reported (Virella et al., 2004). Coefficients of variation for 50 samples measured in two separate assays were 5.2% for oxLDL, and 8.3% for AGE-LDL. The development of standards for calibration of the oxLDL and AGE-LDL assays, as well as sensitivity, reproducibility, and recovery data for the capture assays have been reported elsewhere (Virella et al., 2005). The levels of the different LDL modifications in human circulating IC were expressed in function of the amount of cholesterol contained in the IC and the final values given as the concentration per mL of serum.

Other Methods.

At the baseline DCCT examination each participant completed a physical examination, medical history, electrocardiogram and laboratory testing including serum creatinine, lipid profile and hemoglobin A1c (Epidemiology of Diabetes Interventions and Complications (EDIC), 1999; The Diabetes Care and Complications Trial (DCCT) Research Group, 1987). Four-hour urine collections for measurement of albumin excretion rate and creatinine clearance were also obtained during EDIC in alternate years (Epidemiology of Diabetes Interventions and Complications (EDIC), 1999; The Diabetes Care and Complications Trial (DCCT) Research Group, 1987). Baseline covariates for the current analyses were obtained from DCCT baseline history, physical examination and laboratory data (fasting lipids and renal function). The methodology used to perform all the routine measurements used as conventional risk factors in this study have been performed as part of the DCCT/EDIC study and have been described elsewhere as mentioned above (Epidemiology of Diabetes Interventions and Complications (EDIC), 1999; The Diabetes Care and Complications Trial (DCCT) Research Group, 1987; The Diabetes Care and Complications Trial (DCCT) Research Group, 1986).

Statistical Analysis.

Standard descriptive statistics were used to summarize the general demographic and clinical data. A Wilcoxon Rank Sum test was used to compare continuous demographic and clinical measures between nephropathy prone and resistant subjects. Pearson chi-square test was used to compare categorical variables between the nephropathy prone and resistant groups.

From the 1441 subjects randomized at the DCCT baseline, two subsets were selected post hoc to comprise the sample of the 302 nephropathy resistant and the 82 nephropathy prone, and thus, there was the potential that "confounding" had been introduced into the study sample by the selection process. To minimize the effects of "confounding" on the analysis, conditional (stratified) logistic regression was used to quantify the association of modified LDL-IC levels with subsequent development of albuminuria/nephropathy (Agresti, 2002). Baseline AERs values were grouped into deciles, and the deciles were used as a stratification variable in the conditional logistic regression model. It should be noted that in conditional logistic regression, the effects of baseline AER levels have been removed ("conditioned") out of the estimation process in a manner similar to a stratified Cox regression (Prentice and Pyke, 1979). The primary parameter of interest in the conditional logistic regression models was the change in the log-odds (with 95% Wald CI) for the development of albuminuria/diabetic nephropathy for the main effect of baseline natural-log-transformed modified LDL-IC levels after controlling for DCCT randomized treatment, retinopathy cohort at DCCT baseline (DCCT primary versus secondary cohort), duration of diabetes (months) at DCCT baseline as well as LDL and HbA1c also at DCCT baseline. The modified LDL-IC levels were natural log-transformed to normalize the distribution of the IC levels. Without the transformation, the distributions of IC levels were highly skewed to the right.

To further measure the effect of the modified LDL-IC measurements on the development of albuminuria/diabetic nephropathy, the strength of the association of the covariates was quantified using the change in the -2 log likelihood indices as well as the entropy R-squared ($R^2_E$) (Lachin, 2000). Statistical significance for the change was computed using likelihood ratio tests for nested regression models.

All statistical analyses were performed using the SAS System version 9.2. The type I error rate was controlled at 0.05 for all analysis, and p-values have not been adjusted for multiple comparisons.

Example 5

Results

Demographic and clinical differences between nephropathy groups at baseline measurement are summarized in Table 4. There were statistically significant differences in several clinical factors such as duration of diabetes at study entry, albumin excretion rate, HbA1C %, and mild retinopathy at DCCT Baseline (DCCT primary vs. secondary cohort indicator), and HDL at DCCT Baseline. Many of these findings were expected since both primary and secondary prevention retinopathy cohorts were enrolled and the secondary prevention cohort had a longer duration of DM as well as mild disease at time of randomization. Duration was restricted to 1-5 years duration in the primary and 1-15 in the secondary cohorts. There was also a statistically significant difference in the length of follow up between those deemed nephropathy prone as compared to those deemed nephropathy resistant. The difference, however, is roughly one half of a year and is not considered clinically relevant. It is also noted that the mean time to be considered nephropathy prone was found to be 8.45 years (SD=4.05; IQR=5.0-11.3), and 64 (78.1%) of the event times were at less than 12 years of follow up.

There were also mild differences in total cholesterol, LDL cholesterol, and gender. Both Oxidized LDL-IC levels and AGE LDL-IC at DCCT baseline were higher in the nephropathy prone group than the resistant group (5.1±0.8 vs. 4.6±0.9, $p<0.01$ and 1.7±0.9 vs. 1.3±1.1, $p=0.003$ respectively). Since the modified LDL-IC levels were hypothesized to be the determinant factor and the estimation of the modified LDL-IC levels were scaled based on total cholesterol level, no cholesterol differences were used as adjustment variables in the analysis even though baseline differences were observed.

In unadjusted conditional logistic analysis, an increase of 0.9 (1SD) in the log-transformed oxLDL-IC increased the odds of subsequent development of nephropathy by a factor of 2 (OR=2.0 (1.5-2.7), $p<0.001$). This point estimate remained relatively stable and highly significant with the addition of the adjustment variables (Adj. OR=1.9 (1.4-2.8), $p=0.001$) (FIG. 4A). Similarly, the unadjusted analysis of a 1.04 (1SD) in the AGE LDL-IC increased the odds of development of nephropathy by a factor of 1.5 (OR=1.5 (1.1-2.0), $p=0.005$). With the addition of the covariates, the effect of AGE LDL-IC remained significant (OR=1.5 (1.2-2.0), $p=0.021$). The adjustment variables HbA1C % and DCCT Treatment group were also statistically significant ($p<0.001$) in both models (Table 5).

A trend towards a significant interaction of the DCCT treatment group and oxLDL-IC levels was observed. The p-value of the interaction term was variable depending on which main effects were included in the regression model, but the point estimates of the interaction terms remained relatively stable across models. In a conditional logistic regression model that consisted of the DCCT treatment group, oxLDL levels in IC, and their interaction ($p=0.09$). The magnitude of the parameter estimate decreased after the addition of the baseline factors ($p=0.17$), which is an indication of weak confounding. However the results do still convey an important moderation effect of treatment (FIG. 4B). A 1 SD increase in oxLDL-IC yielded a significant increase for the odds of nephropathy in the group on conventional diabetes therapy (OR=2.3 (1.5-3.5), $p<0.001$), but the intensively-treated participants had a non-significant increase for the same increase (OR=1.4 (0.7-2.5), $p=0.34$). The interaction effect of AGE-LDL levels in IC and DCCT treatment group was less pronounced ($p=0.42$).

In order to determine the strength of association of the covariates in the model with the nephropathy outcome, likelihood ratio tests were performed for the full models against the model with only the three adjustment variables included as well as a model with only DCCT Treatment group assignment as a predictor (Table 6). The model with only DCCT treatment group assignment predicting nephropathy outcomes attained a −2 log likelihood of 307.1 (1 parameter estimated) while that of the model with the addition of primary retinopathy at baseline, baseline diabetes duration, baseline LDL, and HbA1C % had a significantly lower value of 240.4 (5 parameters estimated; $p<0.001$). When the LDL-IC measures were (individually) included in the model, a significant increase in model fit was achieved. With the inclusion of AGE LDL-IC, the −2 log likelihood was 229.2 and 226.1 with the inclusion of oxLDL-IC (6 parameters estimated; $p<0.001$ for both). Thus, the addition of the biomarkers to the predictive model betters the model fit over the inclusion of the preliminary indicators alone. The AER stratified conditional model with only DCCT treatment group assignment had a likelihood ratio chi-square of 24.3 ($p<0.001$) by itself with an approximate $R^2_E$ of 0.073. When primary retinopathy at baseline, baseline diabetes duration, baseline LDL, and HbA1C % were added to the model, the joint chi-square was 66.7, $p<0.001$ with an $R^2_E$ of 0.217. When the LDL IC measures were (individually) added to the model with the 5 covariates, a significant increase in model fit was achieved. The chi-square test of the addition of AGE LDL-IC was 11.2, $p=0.001$, $R^2_E=0.254$, and that for the addition of oxLDL-IC was 14.3, $p<0.001$ $R^2_E=0.264$. Thus, the addition of the biomarkers improved the fit of the model with the other covariates.

Example 6

Discussion

The effect of lipids and lipoproteins in the development of nephropathy has recently been the object of close attention and the contribution of dyslipidemia to the development of nephropathy is well established (Lopes-Virella et al., 2008; Seliger, 2006). The role of immune complexes in the pathogenesis of nephropathy is also well established, although most of the examples have been in glomerulopathies other than diabetic nephropathy (Ambrus and Sridhar, 1997; Mann and Neilson, 1985). The possible involvement of IC in the pathogenesis of diabetic nephropathy had been suggested by us (Virella et al., 1981) and others (Nicoloff et al., 2004) in studies based on non-specific assays for IC, later supported by data generated using assays in which the LDL content of isolated IC was measured (Atchley et al., 2002; Yishak et al., 2006). The data presented in this study clearly shows that higher baseline AGE and oxLDL levels in isolated IC were associated with increased odds to develop diabetic nephropathy in the DCCT/EDIC cohort.

Several points need to be considered in this study. Approximately equal numbers of patients from a primary and a secondary cohort were enrolled in the DCCT study. The primary cohort had no complications and the secondary cohort had mild to moderate retinopathy and AER values between 41 and 200 mg/24 hr. Also there was a difference in diabetes duration between the two groups (1-5 years in the primary group and 1-15 years in the secondary group). Since the inventors could not examine the whole cohort and the number of patients who developed abnormal albuminuria up to EDIC year 9 was relatively small, they studied all the patients with albuminuria (cases), defined as having an AER >60 mg/24 hr at least in two successive determinations and studied 3-4 patients with normal AER (controls) per case. The selection was random but due to the pre-selection criteria the subgroup of cases included more patients enrolled as part of the secondary prevention in the DCCT study. Patients with albuminuria approximately 20 years later included, as expected, a larger number of patients enrolled as part of the secondary prevention group. Therefore the frequency of retinopathy, AER values, and duration of diabetes were higher at baseline in the group considered prone to nephropathy compared to the group resistant to nephropathy. This analysis was appropriately adjusted for all these factors.

Interestingly a lower level of HDL cholesterol and a higher level of triglycerides and total cholesterol, as well as elevated HbA1c were observed in the group prone to nephropathy although at entrance into the study the levels of these parameters in the primary and secondary prevention subgroups were similar. As part of the DCCT design lipid levels were "normal" to qualify for enrollment. However, even at baseline a slight but significant increase of triglycerides and total cholesterol as well as a lower HDL-cholesterol level was observed in the patients prone to nephropathy. No significant difference was however observed in LDL-C levels. Interestingly, both cholesterol and triglycerides as well as HDL-cholesterol levels are well within "normal limits" in both groups. LDL-Cholesterol was, by present guidelines, slightly elevated in both groups although not significantly different. This is not the case for HbA1c were the levels are quite abnormal in the group prone to nephropathy and the difference in absolute levels between the two groups is considerably higher than that observed in lipid levels. When the interaction of DCCT treatment group and oxLDL concentration in isolated IC was considered, a significant increase in the odds to develop nephropathy was clearly observed in the group of patients treated conventionally but not in the group treated intensively. The interaction between DCCT treatment and AGE-LDL levels in IC was less marked. Thus, higher baseline oxLDL levels in IC were associated with increased odds to develop abnormal albuminuria and eventually progression to nephropathy in the conventionally treated patients and the increase in odds to develop abnormal albuminuria was quite similar to that observed with high levels of HbA1c. In contrast, higher baseline LDL-C levels were not associated with increased odds to develop abnormal albuminuria. In other words, the level of oxLDL in IC measured in conventionally treated patients is as good predictor for the development of nephropathy as HbA1c. Interestingly the predictive value of oxLDL in IC appears to be moderated by intensive therapy during DCCT suggesting that optimization of glycemia impacts the formation of oxLDL-IC, likely due to a reduction in oxidative stress and therefore reduction of LDL modification.

The fact that patients with IDDM have circulating IC containing AGE-modified and oxidized LDL strongly suggests a new mechanism by which AGE modification and oxidation of LDL can be significantly involved in the early stages of diabetic nephropathy. These circulating oxLDL- and AGE-LDL-IgG antibodies can easily diffuse to the extravascular space thus favoring the formation of pro-inflammatory IC in the vessel walls both in the kidneys and in other areas of the systemic circulation.

The deposition of AGE-modified proteins starts very early in the evolution of diabetes (McCance et al., 1993), and perhaps as a consequence of local oxidative stress, oxidized proteins are also generated and co-localize with AGE-modified proteins in the expanded mesangium and glomerular capillary walls of patients with diabetic nephropathy (Horie et al., 1997). Among all the modified proteins that can emerge as a consequence of glycooxidation and lipid peroxidation, LDL seems to be particularly important. Studies in animal models and humans suggested that macrophages and hypercholesterolemia played a key role in the evolution of the glomerulosclerosis (Diamond, 1991). The obvious implication would be that hyperlipidemia, common in patients with diabetes, was linked to the development of diabetic nephropathy. It seems likely that hyperlipidemia will facilitate the infiltration of LDL into the extravascular space, including the glomerular mesangium. Activated mesangial cells have been shown to oxidize LDL in vitro (Wheeler et al., 1994). This observation has significant implications, because in situ oxidation of LDL would create the necessary conditions for the formation of oxLDL-IC in the glomeruli. The activation of mesangial cells by IC containing modified LDL is particularly significant in the context of diabetic nephropathy in IDDM, because mesangial expansion seems to be the earliest morphological evidence of the transition to microalbuminuria (Fioretto et al., 1995). As the lesions progressed, inflammatory cells would be recruited and activated leading to the release of pro-inflammatory cytokines and growth factors, followed by a self-perpetuating cycle of mesangial cell activation and proliferation of mesangial cells and expansion of the extracellular matrix resulting in glomerulosclerosis (Diamond, 1991; French et al., 1967; Gin et al., 2000).

Further studies are needed to clearly detail the pathogenic mechanisms by which oxLDL- and AGE-LDL-IC lead to diabetic nephropathy but the present study provides strong clinical evidence that a link may likely exist between the formation and/or deposition in the glomeruli of IC containing AGE or ox-LDL and the initiation and perpetuation of renal disease in patients with type 1 diabetes.

TABLE 4

Descriptive and clinical summary of Type I Diabetes nephropathy prone/resistant patients.

| Variable (DCCT Baseline) | Nephropathy Resistant n = 302 | | Nephropathy Prone n = 82 | | Wilcoxon P Value |
|---|---|---|---|---|---|
| | Mean | Std Deviation | Mean | Std Deviation | |
| Age at Entry | 27.54 | 6.70 | 26.35 | 7.79 | 0.371 |
| Duration of Diabetes at entry | | | | | |
| (Mo) | 61.94 | 49.32 | 78.68 | 45.91 | 0.001 |
| Body Mass Index (kg/m2) | 23.32 | 2.66 | 23.76 | 3.11 | 0.316 |
| Weight (kg) | 69.11 | 11.52 | 69.97 | 14.44 | 0.545 |
| Height (cm) | 171.78 | 9.62 | 170.81 | 11.43 | 0.730 |
| Years of Follow up | 14.51 | 1.98 | 15.02 | 2.38 | 0.005 |
| Mean Arterial Pressure | 86.47 | 8.90 | 87.66 | 7.11 | 0.254 |
| Diastolic BP (mm Hg) | 72.69 | 9.36 | 74.15 | 7.20 | 0.226 |
| Systolic BP (mm Hg) | 114.02 | 11.25 | 114.68 | 10.26 | 0.536 |
| AER (mg/24 hr) | 11.34 | 7.34 | 16.35 | 9.00 | <0.001 |
| HbA1c | 8.45 | 1.42 | 10.00 | 1.68 | <0.001 |
| Serum Creatinine (mg/dl) | 0.82 | 0.15 | 0.78 | 0.16 | 0.075 |
| Triglycerides (Serum, mg/dl) | 73.26 | 36.34 | 97.71 | 45.66 | <0.001 |
| Cholesterol (mg/dl) | 172.59 | 32.70 | 180.04 | 32.59 | 0.045 |
| HDL | 51.67 | 12.10 | 49.01 | 13.93 | 0.027 |

TABLE 4-continued

Descriptive and clinical summary of Type I Diabetes nephropathy prone/resistant patients.

| Variable (DCCT Baseline) | Nephropathy Resistant n = 302 | | Nephropathy Prone n = 82 | | Wilcoxon P Value |
|---|---|---|---|---|---|
| | Mean | Std Deviation | Mean | Std Deviation | |
| LDL | 106.31 | 29.40 | 111.67 | 28.71 | 0.078 |
| Log OxLDL-IC | 4.61 | 0.88 | 5.13 | 0.77 | <0.001 |
| Log AGE-IC | 1.28 | 1.06 | 1.66 | 0.86 | 0.003 |

| | n | % | n | % | Chi Square P Value |
|---|---|---|---|---|---|
| % Male | 158 | 52.3 | 54 | 65.9 | 0.029 |
| % Current Smoker | 63 | 20.9 | 21 | 25.6 | 0.270 |
| % Current Drinker | 61 | 20.2 | 15 | 18.3 | 0.701 |
| % Primary Retinopathy group at Baseline | 166 | 55 | 28 | 34.2 | <0.001 |

TABLE 5

Conditional Logistic Regression Results for Development of Diabetic Nephropathy

| Variable | Unadjusted Model[b] | | Adjusted Model[b] | |
|---|---|---|---|---|
| | OR | P | OR | P |
| Model 1 | | | | |
| Ox LDL-IC[a] | 2.01 (1.49-2.69) | <0.001 | 1.95 (1.35-2.80) | 0.001 |
| Experimental Treatment Group | — | | 0.18 (0.09-0.38) | <0.001 |
| Baseline HbA1C % | — | | 2.11 (1.68-2.64) | <0.001 |
| Primary Retinopathy Group | — | | 0.58 (0.24-1.39) | 0.217 |
| Diabetes Duration (months) | — | | 1.00 (0.99-1.01) | 0.397 |
| LDL | — | | 0.99 (0.98-1.00) | 0.055 |
| Model 2 | | | | |
| AGE LDL-IC[a] | 1.48 (1.13-1.95) | 0.005 | 1.46 (1.06-2.02) | 0.021 |
| Experimental Treatment Group | — | | 0.15 (0.07-0.32) | <0.001 |
| Baseline HbA1C % | — | | 2.14 (1.71-2.68) | <0.001 |
| Primary Retinopathy Group | — | | 0.58 (0.24-1.39) | 0.221 |
| Diabetes Duration (months) | — | | 1.00 (0.99-1.01) | 0.349 |
| LDL | — | | 1.00 (0.98-1.00) | 0.151 |

[a]OR listed for a 1 standard deviation change in natural logged value
[b]Models are stratified on AER Deciles.

TABLE 6

Model Fit Statistics for Conditional Logistic Regression Model for the Development of Diabetic Nephropathy.

| | Conditional Logistic Results | | |
|---|---|---|---|
| Model | −2 Log Likelihood, Parameters | | $R^2_E$[a] |
| DCCT Treatment | 307.1, 1 | | 0.073[†] |
| Covariates Only[b] | 240.4, 5[§] | 0.217[α] | 0.275[†] |
| AGE LDL-IC Full | 229.2, 6[§+] | 0.254[α] | 0.308[†] |
| Ox LDL-IC Full | 226.1, 6[§+] | 0.264[α] | 0.318[†] |

[a]$R^2_E$ is a measure of improvement in the Model fit. It is similar to the standard $R^2$ in that it measures the percentage change in the Log Likelihood attributable to the variables added to the model.
[b]Covariates include DCCT Treatment Group, Primary Retinopathy Group at Baseline, Diabetes Duration at Baseline, LDL at baseline, and HbA1C %.
[†]As compared to intercept only model
[α]As compared to DCCT Treatment only model
[§]P < 0.001 Improvement in fit with the additional variables added to the treatment group model
[+]p < 0.001 Improvement in fit with the additional variables added to the covariate only model Example 7

Materials and Methods

Patients.

This study was performed on a subgroup of 476 subjects from the DCCT/EDIC cohort who had oxLDL-IC levels measured on samples obtained at entry into the DCCT as well as coronary artery calcification (CAC) scores performed during the EDIC phase of the study (11-20 years after enrollment in the DCCT), as a marker for coronary artery disease (CAD) (Cleary et al., 2006). The original DCCT cohort included 1,441 patients who were 13-39 years of age and had type 1 diabetes for 1-15 years at study entry (The Diabetes Control and Complications Trial Res. Group, 1993). The DCCT cohort was randomized to intensive or conventional insulin therapy and followed for an average of 6.5 years. In 1993, the interventional phase of the study was stopped and in 1994, the observational phase of the DCCT/EDIC study (EDIC phase) was initiated (Epidemiology of Diabetes Interventions and Complications (EDIC), 1999), aimed at assessing the development of macrovascular disease in type 1 diabetes. During the EDIC phase, all of the patients were under the care of their personal health care provider and were encouraged to practice intensive insulin therapy. At DCCT Baseline (1983-1989), none of the patients had hypertension (defined as ≥140 and/or ≥90 mmHg) or dyslipidemia (defined as total cholesterol>200 and/or LDL>160 mg/dl).

Of the 1,441 DCCT participants, 90-95% entered the EDIC study and 905 of these individuals had blood collected longitudinally as part of a sub-study on biomarkers of macrovascular disease. From these 905 subjects, 518 patients were selected for measurement of oxLDL-IC. In the selection of these 518 patients, cases of albuminuria, elevated carotid artery intima-media thickness and retinopathy were oversampled (i.e., all available cases were sampled) resulting in 157 of the 518 patients having one of these three endpoints and 361 of the 518 patients having none of these endpoints. Of the 518 with oxLDL-IC measured 476 also had CAC measured during EDIC (Hodis et al., 1998).

Serum samples were obtained after an overnight fast at entry into the DCCT study (between 1983-89). The DCCT and EDIC studies were approved by the Institutional Review Board of all participating DCCT/EDIC centers and all participants provided written informed consent.

Assessment of Coronary Artery Calcification.

CAC was determined by computed tomography (CT), performed 7-9 years after the end of the DCCT in 1,205 (86%) of the surviving 1,404 participants. CT was performed using a C-150 cardiac-gated electron beam CT scanner (n=9; Imatron, San Francisco, Calif.), a Lightspeed (n=7; General Electric Medical Systems, Waukesha, Wis.) or a Volume Zoom (Siemens, Erlanger, Germany) multidetector CT system, a Lightspeed Marconi MX-8000 (GE), or a Somatom 4+ (Siemens) (n=3). All participants were scanned twice over calibration phantoms of known physical calcium concentration. Scans were read centrally at the Harbor-UCLA (University of California, Los Angeles) Research and Education Institute (Torrance, Calif.) to identify and quantify CAC. The average score from the two scans was used in the analysis. Readers were masked to subject identity and prior treatment assignment. Details concerning standardization and reliability of the CAC measurement have been previously published (Cleary et al., 2006).

OxLDL-IC Measurement.

The inventors measured oxLDL by first precipitating circulating immune complexes from serum and then fractionating these IC by protein G affinity chromatography, separating the predominant IgG antibody from modified LDL, as previously described (Atchley et al., 2002; Virella et al., 2004). The concentration of OxLDL in the IC was then assayed with a capture assay developed in the inventors' laboratory using a specific oxLDL antibody (Virella et al., 2005). The development of standards for calibration of the oxLDL assay, as well as sensitivity, reproducibility, and recovery data for the capture assay have been reported elsewhere (Virella et al., 2005). The effect of long term freezing at −70° C. was carefully assessed and found to have no effect in the measurements performed. The levels of oxLDL in human circulating IC were expressed in function of the amount of apolipoprotein B contained in the IC and the final values were given as the concentration per mL of serum Other Procedures.

At the baseline DCCT examination, each participant completed a physical examination, medical history, electrocardiogram and laboratory testing including serum creatinine, and hemoglobin (Atchley et al., 2002; The Diabetes care and Complications Trial (DCCT) Research Group, 1987). Lipid profiles and 4-hour urine collections for measurement of AER and creatinine clearance were also obtained. Covariates for the current analyses were obtained from DCCT baseline history, physical examination and laboratory data (fasting lipids, renal function, and hemoglobin A1c). The methodology used to perform the routine measurements used as conventional risk factors in this study were guided by the DCCT/EDIC study protocols and have been described elsewhere as mentioned above (Epidemiology of Diabetes Interventions and Complications (EDIC), 1999; The Diabetes care and Complications Trial (DCCT) Research Group, 1987). Retinopathy was assessed by obtaining stereo fundus photographs in all participants (Early Treatment Diabetic Retinopathy Study Res. Group, 1991).

Statistical Analysis.

In the analyses performed oxidized LDL-IC at DCCT baseline was used to determine a person's exposure status and CAC levels 11-20 years later were the outcomes of interest. Values of oxLDL-IC were log transformed due to their skewed, non-normal distribution. The study population was divided into those with minimal to moderate CAC scores (Low Group: <100 Agatston units) and those with increased to extensive CAC scores (High Group: ≥100 Agatstons units) (Greenland et al., 2007; Hoffmann et al., 2003) Standard descriptive and clinical characteristics at DCCT baseline were summarized for the entire study population as well as stratified by CAC outcome. A two-sided Wilcoxon Ranks Sum test was used to compare continuous descriptive and clinical measures between CAC groups. All categorical measures were compared using Pearson's Chi-Square test statistic or Fishers Exact Test when appropriate. The Cochran-Armitage test for trend was used to assess the overall linear trend in the proportion of participants with high CAC scores across the tertiles of oxLDL-IC (chosen for ease of representation).

Due to the skewed nature of the CAC scores, unadjusted and multivariable log-binomial (Relative Risk) regression models with robust error variance estimates (Zou, 2004) were used to estimate the risk ratios associated with the prevalence of high CAC scores with an increase of one standard deviation of the natural logarithm of oxLDL-IC (1 SD=0.9137 mg/L). Risk Models were analyzed both unadjusted and adjusted for DCCT randomized treatment group, baseline age, gender, duration of type 1 diabetes, HbA1C %, CT scanning location, DCCT baseline retinopathy cohort (primary vs. secondary), and AER (mg/24 hr). Further multivariable models looked at the addition of baseline systolic blood pressure, baseline smoking status and baseline LDL-Cholesterol.

Multivariable Tobit regression models were used to examine the association of the observed continuous CAC scores with oxLDL-IC. Calcification scores of zero were assumed immeasurable (but present) and censored. All non-zero CAC scores were natural log transformed and decreased by subtracting the natural logarithm of the lowest detectable CAC score prior to model fitting. Tobit models were implemented using maximum likelihood methods to adjust for this apparent left censoring of the CAC distribution (Tobin, 1958). This method provided a single association measure between oxLDL-IC measures and CAC scores (Reilly et al., 2004). Tobit regression models used in the analysis were fit using the QLIM Procedure in SAS 9.2 and were adjusted for the same covariates as in the risk ratio models.

All statistical analyses were performed using the SAS System version 9.2 (SAS Institute, Cary, N.C., USA). A type I error rate was controlled for significance at 0.05 for all analysis, and p-values have not been adjusted for multiple comparisons.

Example 8

Results

For descriptive purposes, oxLDL-IC was broken into tertiles and Table 7 shows the baseline demographics and clinical data of the patients in each tertile. Increases in oxLDL-IC were associated with increases in the duration of type 1 diabetes, length of DCCT follow-up, cholesterol (s), and baseline AER. Those with higher oxLDL-IC were more likely to have been in the standard treatment group and to be male. The correlation of oxLDL-IC with LDL-cholesterol level, while statistically significant, was of moderate magnitude (Rho=0.22, p<0.001). Comparison of DCCT baseline characteristics of the 476 participants included in the current study and those of the 965 participants excluded revealed longer duration of diabetes, higher body mass index and higher AER in the participants included into the study compared to those excluded. Those included were also less likely to be in the primary retinopathy cohort. Included and excluded participants were of similar age and sex, were similarly likely to smoke and drink alcohol and had similar lipid, blood pressure and hemoglobin A1c measures at baseline.

Demographic and clinical differences between CAC groups (0-100 and >100) are summarized in Table 8. At DCCT baseline, the mean age of the study population (n=476) was 27.2±7.0 years, the mean duration of diabetes was 5.8±4.1 years, 52.3% (n=249) were males, 97.3% (n=463) were Caucasian and 45.6% (n=217) were assigned to the DCCT intensive treatment group. In the high CAC group, duration of type 1 diabetes was higher (5.7±4.1 vs. 6.9±4.5, p<0.001) and the proportion of smokers was higher than in the low CAC group (17.9% vs. 39.1%, p<0.001). LDL-cholesterol, total cholesterol and systolic blood pressure levels as well as the proportion of men were also higher in the high CAC group than the low CAC group.

The overall prevalence of high CAC scores was 14.5% (69/476). The prevalence of having high CAC across oxLDL-IC tertiles is shown in FIG. 5. Prevalence of high CAC scores increases as the levels of oxLDL-IC increase. (Trend P value<0.001).

Table 9 presents the unadjusted and multivariable risk ratios for significant CAC associated with a one standard deviation increase in the natural logarithm of oxLDL-IC. In the unadjusted analysis, those with a one SD change in oxLDL-IC at DCCT baseline had a 51 percent increase in the risk of having a high CAC score (RR=1.51; 95% CI: 1.20-1.88: p<0.001) at follow-up. Once adjusted for common CAC, risk factors and DCCT design variables (DCCT treatment group, baseline retinopathy cohort, baseline diabetes duration, baseline Ln AER, baseline HbA1C %, gender, CT scanning site, and age), the increased risk of a high CAC score associated with the change in oxLDL-IC remained significant (RR=1.36; 95% CI: 1.12-1.67: p=0.003). The addition of LDL, SBP, and smoking status into the model, attenuated the risk ratio slightly, but it remained significant (RR=1.26; 95% CI: 1.03-1.54: p=0.024) and of magnitude only slightly lower than the relative risk associated with a one standard deviation increase in baseline LDL (RR=1.41; 95% CI: 1.17-1.70: p<0.001).

The results of the Tobit regression models were stronger than those from the risk models. In the unadjusted analysis, a one standard deviation increase in oxLDL-IC level resulted in a nearly 3-fold increase in CAC scores (2.98: 95% CI: 1.59-5.59: $X^2$=11.68, p<0.001). Adjustment for common CAC, risk factors and DCCT design variables, attenuated the association somewhat, but a greater than 2-fold increase in mean CAC scores remained (2.15: 95% CI: 1.24-3.72: $X^2$=7.43, p=0.006). Further adjustment for LDL levels, SBP, and smoking status, further attenuated the effect of baseline oxLDL-IC on CAC score (1.63: 95% CI: 0.95-2.79: $X^2$=3.13, p=0.076). In all fully adjusted models, the possible effect modification of DCCT treatment group, baseline retinopathy cohort, and gender on OxLDL-IC were tested. None were found to be significant and were removed from the model.

Example 9

Discussion

Increased levels of oxLDL-IC at DCCT baseline are associated with an increased risk of having clinically significant coronary artery calcification 11 to 20 years later in patients with type 1 diabetes. When adjustments for different variables were introduced, particularly LDL level, the effect of an increase in oxLDL-IC level was attenuated, the relative risk decreasing from 1.51 to 1.23 but remained statistically significant. As expected, the degree of dyslipidemia, and in particular the levels of LDL-cholesterol did correlate with the levels of oxLDL-IC, because higher levels of LDL will inevitably result in higher levels of oxLDL, the necessary antigen for the formation of oxLDL-IC. In a previous study, the inventors demonstrated that the total LDL particle number as well as the concentrations of both small LDL and large LDL particles (assessed by nuclear magnetic resonance spectroscopy) were responsible for LDL-IC formation in the DCCT/EDIC cohort (Klein et al., 2010).

In the full model, LDL itself remained significant, suggesting, not surprisingly, that it also has an effect on coronary calcification independent of oxLDL-IC. A limitation of the study is the lack of a random sampling. To increase the statistical power available participants were oversampled (i.e., all available cases were sampled) for one of three endpoints none of which are the endpoint for the current report: albuminuria, elevated carotid artery intima-media thickness and retinopathy. To overcome this selection bias throughout all analyses, the inventors have controlled for baseline markers of diabetes severity (i.e., DCCT retinopathy status, diabetes duration, and hemoglobin A1C) and albuminuria (i.e., the case-control selection criteria). Additionally, the inventors determined that neither markers of diabetes severity, albuminuria nor DCCT treatment group were acting as effect modifiers of associations of interest, thus indicating that the predictive ability of IC was similar across different levels of these variables.

Previous publications from the inventors' group and others had pointed to the potential pathogenic role of oxLDL-IC. Orchard et al. reported that levels of LDL-containing IC measured at baseline were directly related to subsequent CAD (Orchard et al., 1999). In a nested case-control study including 49 incident cases of myocardial infarction, angina, or death attributed to CAD and 49 control subjects, matched for age, gender, and duration of diabetes, using multivariate analysis, modified LDL-IC, assessed by measuring the cholesterol content in isolated immune complexes were shown to be independent predictors of CAD. In addition, a complementary study from the inventors' group using the same patient cohort showed that the IC from the patients that developed CAD, contained higher LDL concentrations and higher concentrations of IgG than those measured in IC isolated from control cases (Lopes-Virella et al., 1999). A later study carried out in 1050 patients from the DCCT/EDIC cohort showed that LDL-IC (measured by the concentration of cholesterol and ApoB in precipitated IC) were present in higher levels in patients that showed progression of the intima-media thickening (IMT) over a follow-up period of 4 to 6 years (Lopes-Virella et al., 2007).

Using capture assays for modified LDL, the inventors have also revisited the correlation between modified LDL IC levels and IMT in a DCCT/EDIC cohort of 479 patients who had levels of oxLDL and AGE-LDL IC at DCCT Baseline, and for whom IMT was measured 8-4 years later. After adjusting for treatment group, retinopathy status, age, sex, diabetes duration, hemoglobin A1c and ultrasonography equipment oxLDL-IC and AGE-LDL-IC each significantly predicted internal and common carotid IMT at EDIC year 1 and 6 (unpublished results).

In conclusion, the humoral immune response to modified LDL in humans appears to be a prime factor in the progression of atherosclerosis in humans. The demonstration that increased levels of oxLDL-IC predict the development of coronary artery calcification is a very significant finding supporting previous evidence and pointing to a pathogenic role of modified LDL immune complexes.

TABLE 7

Demographic and clinical characteristics measured at DCCT Baseline by OxLDL-IC Tertile Grouping

| | OxLDL-IC Tertiles | | | | |
| --- | --- | --- | --- | --- | --- |
| | 1<br>n = 158 | 2<br>n = 159 | 3<br>n = 159 | ($\chi^2$)<br>Statistic† | P-Value |
| Age (yrs) | 26.9 ± 6.9 | 27.5 ± 6.6 | 27.3 ± 7.4 | 0.57 | 0.751 |
| Weight (kg) | 67.9 ± 12.7 | 69.5 ± 11.8 | 70.5 ± 12.5 | 3.52 | 0.172 |
| Height (cm) | 171.1 ± 9.6 | 171.3 ± 10.7 | 171.7 ± 9.9 | 0.36 | 0.836 |
| BMI | 23.0 ± 2.8 | 23.5 ± 2.5 | 23.8 ± 3.2 | 5.40 | 0.067 |
| Duration of T1D (yrs) | 5.5 ± 4.1 | 5.6 ± 4.2 | 6.5 ± 4.2 | 6.94 | 0.031 |
| DCCT Follow up (yrs) | 6.1 ± 1.6 | 6.4 ± 1.8 | 6.9 ± 1.8 | 13.47 | 0.001 |
| EDIC Follow up (yrs) | 9.0 ± 0.5 | 9.1 ± 0.5 | 9.1 ± 0.5 | 3.26 | 0.196 |
| SBP (mmHg) | 113.2 ± 11.5 | 115.0 ± 11.0 | 115.6 ± 11.0 | 4.19 | 0.123 |
| DBP (mmHg) | 72.7 ± 9.0 | 72.5 ± 9.2 | 74.3 ± 8.7 | 5.85 | 0.054 |
| MAP (mmHg) | 86.2 ± 9.0 | 86.7 ± 8.6 | 88.1 ± 8.5 | 5.97 | 0.051 |
| Cholesterol | 169.5 ± 29.7 | 171.5 ± 35.1 | 183.3 ± 32.7 | 15.49 | <0.001 |
| HDL | 53.4 ± 12.9 | 49.9 ± 11.7 | 49.0 ± 11.9 | 11.03 | 0.004 |
| LDL | 101.8 ± 26.6 | 106.1 ± 30.8 | 116.5 ± 28.2 | 20.29 | <0.001 |
| Trig | 72.2 ± 31.1 | 77.6 ± 38.9 | 89.2 ± 44.7 | 16.12 | <0.001 |
| HbA1C % | 8.8 ± 1.5 | 8.7 ± 1.6 | 9.1 ± 1.7 | 4.67 | 0.088 |
| AER | 14.9 ± 13.5 | 15.8 ± 21.6 | 18.0 ± 17.8 | 7.60 | 0.022 |
| Serum Creatinine | 0.81 ± 0.16 | 0.80 ± 0.14 | 0.80 ± 0.15 | 1.25 | 0.536 |
| Intensive Treatment, n (%) | 82 (51.9) | 77 (48.4) | 58 (36.5) | 8.37 | 0.015 |
| Primary Ret Cohort | 75 (47.5) | 83 (52.2) | 55 (34.6) | 10.68 | 0.005 |
| Male | 70 (44.3) | 86 (54.1) | 93 (58.5) | 6.70 | 0.035 |
| Smoker (current at BL) | 29 (18.4) | 36 (22.6) | 35 (22.0) | 1.02 | 0.600 |
| Drinker (current at BL) | 35 (22.2) | 24 (15.1) | 34 (21.4) | 3.03 | 0.220 |

Continuous characteristics are denoted as mean ± standard deviation and categorical characteristics are denoted as n (%)
BMI = Body Mass Index, SBP = Systolic Blood Pressure, DBP = Diastolic Blood Pressure, MAP = Mean Arterial Pressure, HDL = High-Density Lipoprotein Cholesterol, LDL = Low-Density Lipoprotein, Trig = triglycerides, AER = Albumin Excretion Rate
†Continuous measures are compared with Wilcoxon Ranks Sum statistics. Pearson Chi Square statistics are used for Categorical measures.

TABLE 8

Demographic and clinical characteristics measured at DCCT Baseline by CAC Grouping

| DCCT Baseline | | CAC Groupings | | | |
| --- | --- | --- | --- | --- | --- |
| Characteristic<br>(Mean ± SE) | Overall<br>N = 476 | 0-100<br>n = 407 | >100<br>n = 69 | (Z)<br>Statistic† | P-Value |
| Age (yrs) | 27.2 ± 7.0 | 26.5 ± 6.8 | 31.7 ± 5.9 | 5.9 | <0.001 |
| Weight (kg) | 69.3 ± 12.4 | 68.5 ± 11.9 | 74.2 ± 14.0 | 3.2 | 0.002 |
| Height (cm) | 171.4 ± 10.1 | 171.0 ± 10.2 | 173.8 ± 8.7 | 2.6 | 0.011 |
| BMI | 23.5 ± 2.8 | 23.3 ± 2.8 | 24.4 ± 3.1 | 2.6 | 0.009 |
| Duration of T1D (yrs) | 5.8 ± 4.1 | 5.7 ± 4.1 | 6.9 ± 4.5 | 2.1 | 0.036 |
| SBP (mmHg) | 114.6 ± 11.2 | 114.0 ± 11.3 | 117.9 ± 10.3 | 2.6 | 0.009 |
| DBP (mmHg) | 73.2 ± 9.0 | 73.1 ± 9.1 | 73.9 ± 8.1 | 0.8 | 0.431 |
| MAP (mmHg) | 87.0 ± 8.7 | 86.7 ± 8.8 | 88.5 ± 7.9 | 1.7 | 0.090 |
| Cholesterol | 174.8 ± 33.1 | 172.1 ± 32.2 | 190.7 ± 34.0 | 4.4 | <0.001 |
| HDL | 50.7 ± 12.3 | 51.2 ± 12.4 | 47.9 ± 11.3 | −1.9 | 0.056 |
| LDL | 108.1 ± 29.2 | 105.2 ± 28.1 | 125.7 ± 29.6 | 5.5 | <0.001 |
| Trig | 79.7 ± 39.2 | 78.6 ± 39.4 | 85.9 ± 37.8 | 1.8 | 0.067 |
| HbA1C % | 8.9 ± 1.6 | 8.8 ± 1.6 | 9.0 ± 1.7 | 0.7 | 0.463 |
| AER | 16.3 ± 17.9 | 15.7 ± 15.6 | 19.8 ± 28.1 | 1.3 | 0.180 |
| Serum Creatinine | 0.80 ± 0.15 | 0.80 ± 0.15 | 0.81 ± 0.15 | 0.6 | 0.507 |
| OxLDL-IC at DCCT Entry | 5.03 ± 0.91 | 4.98 ± 0.92 | 5.38 ± 0.81 | 3.5 | <0.001 |
| Intensive Treatment, n (%) | 217 (45.6) | 189 (46.4) | 28 (40.6) | 0.8 | 0.366 |

TABLE 8-continued

Demographic and clinical characteristics measured at DCCT Baseline by CAC Grouping

| DCCT Baseline | | CAC Groupings | | | |
|---|---|---|---|---|---|
| Characteristic (Mean ± SE) | Overall N = 476 | 0-100 n = 407 | >100 n = 69 | (Z) Statistic† | P-Value |
| Primary Ret Cohort | 213 (44.8) | 189 (46.4) | 24 (34.8) | 3.2 | 0.072 |
| Male | 249 (52.3) | 200 (49.1) | 49 (71.0) | 11.3 | <0.001 |
| Smoker (current at BL) | 100 (21.0) | 73 (17.9) | 27 (39.1) | 16.1 | <0.001 |
| Drinker (current at BL) | 93 (19.5) | 77 (18.9) | 16 (23.2) | 0.7 | 0.406 |

Continuous characteristics are denoted as mean ± standard deviation and categorical characteristics are denoted as n (%).
BMI = Body Mass Index, SBP = Systolic Blood Pressure, DBP = Diastolic Blood Pressure, MAP = Mean Arterial Pressure, HDL = High-Density Lipoprotein Cholesterol, LDL = Low-Density Lipoprotein, Trig = triglycerides, AER = Albumin Excretion Rate
†Continuous measures are compared with Wilcoxon Ranks Sum statistics. Pearson Chi Square statistics are used for Categorical measures.

TABLE 9

Unadjusted and Multivariate Relative Risk Regression Results for oxLDL-IC association with High CAC status

| Relative risks associated with risk factors of CAC | Model 1 (Unadjusted) | Model 2 | Model 3 | Model 4 * |
|---|---|---|---|---|
| oxLDL-IC (1 SD Increase) | 1.51 (1.20-1.88) § | 1.36 (1.12-1.67) § | 1.35 (1.10-1.66) § | 1.23 (1.01-1.50) † |
| Baseline LN AER | | 1.17 (0.89-1.54) | 1.13 (0.86-1.48) | 1.11 (0.83-1.47) |
| Experimental Treatment Group | | 0.95 (0.61-1.47) | 0.94 (0.60-1.46) | 0.92 (0.59-1.44) |
| Secondary Retinopathy Cohort | | 0.85 (0.45-1.61) | 0.93 (0.49-1.77) | 0.90 (0.46-1.76) |
| HbA1C (1 unit increase, %) | | 1.08 (0.93-1.25) | 1.04 (0.89-1.21) | 1.02 (0.88-1.17) |
| Diabetes Duration at BL(1 year increase) | | 1.07 (1.01-1.15) † | 1.06 (0.99-1.13) | 1.06 (0.99-1.14) |
| Age at BL (1 year increase) | | 1.12 (1.08-1.16) § | 1.11 (1.06-1.15) § | 1.10 (1.06-1.15) § |
| Male (men versus women) | | 1.92 (1.20-3.09) § | 1.96 (1.20-3.19) § | 2.64 (1.39-5.01) § |
| DBP (10 unit increase, mmHg) | | | 0.96 (0.78-1.19) | 1.02 (0.82-1.28) |
| Baseline Smoking (yes vs. no) | | | 1.58 (1.01-2.51) † | 1.48 (0.94-2.33) |
| LDL (1 SD increase) | | | | 1.40 (1.16-1.70) § |

Risk Models:
1: Ox LDL IC only
2: Adjusted for DCCT Treatment Group, Retinopathy Cohort, age, gender, baseline HbA1C %, CT Scanning location, Baseline AER, and Baseline Diabetes Duration.
3: Additionally Adjusted for Smoking Status and Diastolic Blood Pressure
4: Additionally adjusted for baseline LDL
† p < 0.05
§ p < 0.01
* LDL was chosen for model inclusion based on significance within the model. HDL, Cholesterol, and Triglycerides were highly non-significant when included in the model, and were therefore removed from model 4.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference.

U.S. Pat. No. 5,757,994
U.S. Pat. No. 5,788,166
U.S. Pat. No. 5,838,002
U.S. Pat. No. 5,986,258
U.S. Pat. No. RE 35,413
Agresti, In: *Categorical Data Analysis*, John Wiley & Sons, New York, 2002.
Ambrus, Jr. and Sridhar, *Jama*, 278:1938-1945, 1997.
Anderson et al., *Clin. Immunol.*, 102:200-207, 2002
Andersson et al., Adaptive Immunity and Atherosclerosis, *Clin. Immunol.*, [Epub ahead of print], 2009.
Atchley et al., *Diabetologia*, 45:1562-1571, 2002.
Bahr et al., *J. Mass Spectrom.*, 32:1111-1116, 1997.
Bentzley et al., *Anal Chem.*, 68(13):2141-2146, 1996.
Binder et al., *Nature Med.*, 8:1218-1226, 2002.
Bucknall et al., *J. Am. Soc. Mass Spectrom.*, 13(9):1015-1027, 2002.
Burton and Woof, *Adv. Immunol.*, 51:1-84, 1992.
Caprioli et al., *Anal. Chem.*, 69:4751, 1997.
Chaurand et al., *Anal Chem.*, 71(23):5263-5270, 1999.
Chen et al., *Biomed Chromatogr.*, 15(8):518-24, 2001.
Cleary et al., *Epid. Diab. Interven. Complic.* (DCCT/EDIC) Study Diab., 55:3556-65, 2006.
Desiderio et al., *J. Mass Spectrom.*, 35(6):725-733, 2000.
Desiderio et al., *Methods Mol. Biol.*, 61:57-65, 1996.
Diamond, *Kidney Intl.*, 39(suppl):S29-S34, 1991.
Drake et al., *Am. J. Pathol.*, 138:601-607, 1991.

Duncan et al., *Rapid Commun. Mass Spectrom.*, 7(12):1090-1094, 1993.
Early Treatment Diabetic Retinopathy Study Res. Group, ETDRS Rpt. No. 12, *Ophthalmology*, 98(Suppl.):823-833, 1991.
Eckel et al., *Circulation*, 105:138-143, 2002.
Epidemiology of Diabetes Interventions and Complications (EDIC) Res. Group, *Diabetes*, 48:383-390, 1999.
Epidemiology of Diabetes Interventions and Complications (EDIC), *Diabetes Care*, 22:99-111, 1999.
Faulstich et al., *Anal. Chem.*, 69(21):4349-4353, 1997.
Fenn et al., *Science*, 246(4926):64-71, 1989.
Fioretto et al., *Kidney Intl.*, 48:1929-1935, 1995.
French et al., *Arch. Pathol. Lab. Med.*, 83:204-210, 1967.
Game et al., *Atherosclerosis*, 169:235-243, 2003.
Gin et al., *Diabetes & Metabolism*, 26:45-53, 2000.
Gobom et al., *Anal. Chem.*, 72(14):3320-3326, 2000.
Greenland et al., *J. Am. Coll. Cardiol.*, 49:378-402, 2007.
Hazen, *J. Biol. Chem.*, 283(23):15527-15531, 2008.
Hodis et al., *Ann. Intern. Med.*, 128:262-269, 1998.
Hoffmann et al., *Circulation*, 108:e50-3, 2003.
Horak et al., *Rapid Commun. Mass Spectrom.*, 15(4):241-248, 2001.
Horie et al., *J. Clinical Investig.*, 100:2995-3004, 1997.
Ikeda et al., *J. Immunol. Methods*, 215(1-2):95-104, 1998.
Jespersen et al., *Anal Chem.*, 71(3):660-666, 1999.
Jiang et al., *Biochem. Pharmacol.*, 59:763-772, 2000.
Kabarle et al., *Anal. Chem.* 65(20):972A-986A, 1993.
Kanazawa et al., *Biol. Pharm. Bull.*, 22(4):339-346, 1999.
Kazmaier et al., *Anesthesiology*, 89(4):831-817, 1998.
Klein et al., *J. Diabetes Complications*, 2010. [Epub ahead of print]
Kusuhara et al., *Arterioscler. Thromb. Vasc. Biol.*, 17(1):141-148, 1997.
Lachin, In: Biostatistical Methods. *The Assessment of Relative Risks*, John Wiley & Sons, NY, 2000.
Liao et al., *J. Clin. Invest.*, 87:2253-2257, 1991.
Libby, *Nature*, 420(6917):868-874, 2002.
Liedtke, In: *A Mechanism of a Metabolic Induction of Coronary Artery Disease in Chronic Kidney Disease*, Pharmed Institute of Cybernetics, PIC. Res. Comm., 2008.
Lopes-Virella et al., *Ann. NY Acad. Sci.*, 367-378, 2005.
Lopes-Virella et al., *Atherosclerosis*, 190(2):359-369, 2007.
Lopes-Virella et al., *Clin. Immunol.*, 90(2):165-172, 1999.
Lopes-Virella et al., *Diabetes Care*, 31:2006-2012, 2008.
Lovelace et al., *J. Chromatogr.*, 562(1-2):573-584, 1991.
Lynn et al., *J. Mol. Evol.*, 48(5):605-614, 1999.
Mann and Neilson, *Med. Clin. North Am.*, 69:715-750, 1985.
Marie et al., *Anal. Chem.*, 72(20):5106-5114, 2000.
McCance et al., *J Clin. Invest.*, 91:2470-2478, 1993.
Michaelsen et al., *Scand. J. Immunol.*, 70:553-564, 2009.
Miketova et al., *Mol. Biotechnol.*, 8(3):249-253, 1997.
Mirgorodskaya et al., *Rapid Commun. Mass Spectrom.*, 14(14):1226-1232, 2000.
Mironova et al., *Arterioscler. Thromb. Vasc. Biol.*, 16:222-229, 1996.
Muddiman et al., *Fres. J Anal. Chem.*, 354:103, 1996.
Nakamura et al., *Am. J. Pathol.*, 143:1649-1656, 1993.
Nathan et al., *N. Engl. J. Med.*, 348:2294-2303, 2003.
Nelson et al., *Rapid Commun. Mass Spectrom.*, 8(8):627-631, 1994.
Nguyen et al., *J. Chromatogr. A.*, 705(1):21-45, 1995.
Nicoloff et al., *Clin. Dev. Immunol.*, 11:61-66, 2004.
Onorato et al., *Ann. NY Acad. Sci.*, 854:277-290, 1998.
Orchard et al., *Diabetes*, 48(7):1454-1458, 1999.
Palinski et al., *Proc. Natl. Acad. Sci. USA*, 86:1372-1376, 1989.
Prentice and Pyke, *Biometrika*, 66:403-411, 1979.
Quinn et al., *Proc. Nat. Acad. Sci. USA*, 84:2995-2998, 1987.
Reilly et al., *Atherosclerosis*, 173:69-78, 2004.
Requena et al., *Biochem. J*, 322:317-325, 1997.
Roepstorff, In: *MALDI-TOF Mass Spectrometry Protein Chemistry*, Jolles and Jörnvall (Eds.), 1-220, 2000.
Ross, *N. Eng. J Med.*, 340(2):115-126, 1999.
Saad et al., *J. Lipid. Res.*, 47(9):1975-1983, 2006.
Schmidt et al., *J. Clin. Invest.*, 96(3):1395-1403, 1995.
Seliger, *Kidney Intl.*, 69:206-208, 2006.
Steinberg, *Nature Med.*, 8:1211-1217, 2002.
Steinbrecher et al., *J. Lipid Res.*, 25:1109-1116, 1984.
Steinbrecher, *J. Biol. Chem.*, 262:3603-3608, 1987.
Stemme et al., *Proc. Nat. Acad. Sci. USA*, 92(9):3893-3897, 1995.
Stoeckli et al., *Nat. Med.*, 7(4):493-496, 2001.
Takach et al., *J. Protein Chem.*, 16:363, 1997.
Terkeltaub et al., *Arterioscler. Thromb.*, 14:47-53, 1994.
The Diabetes care and Complications Trial (DCCT) Res. Group, Clin. Chem., 33:2267-2271, 1987.
The Diabetes Control and Complications Trial (DCCT), *Diabetes*, 35(5):530-545, 1986.
The Diabetes Control and Complications Trial Res. Group, *New England J. Medicine*, 329(14):977-986, 1993.
Tobin, *J. Relation. Llimited Depend. Variables Econometrica*, 26:24-36, 1958.
Villanueva et al., *Genes Dev.*, 13:3160-3169, 1999.
Virella and Lopes-Virella, *Atherosclerosis*, 200(2):239-246, 2008.
Virella and Lopes-Virella, *Clin. Diag. Lab. Immunol.*, 10:499-505, 2003.
Virella and Tsokos, In: *Immune Complex Diseases*, Virella (Ed.), NY and London: Informa, 323-334, 2007.
Virella et al., *Clin. Diagn. Lab. Immunol.*, 12(1):68-75, 2005.
Virella et al., *Clin. Immunol.* 127(3):394-400, 2008.
Virella et al., *Clin. Immunol.*, 95(2):135-144, 2000.
Virella et al., *Diabetologia*, 21:184-191, 1981.
Virella et al., *J. Lipid Res.*, 44:487-493, 2003.
Virella et al., *J. Lipid Res.*, 45:1859-1867, 2004.
Virella, In: *Biosynthesis, metabolism and biological properties of immunoglobulins*, Virella (Ed.), NY and London: Informa; 65-72, 2007.
Wheeler et al., *Kidney Intl.*, 45:1628-1636, 1994.
Wittmann et al., *Biotechnol. Bioeng.*, 72:642, 2001.
Wu et al., *Anal. Biochem.*, 263(2):129-38, 1998.
Wu et al., *Rapid Commun Mass Spectrom.*, 14(9):756-64, 2000.
Yang et al., *J. Agric. Food Chem.*, 48(9):3990-6, 2000.
Yishak et al., *Nephrol. Dial. Transplant.*, 21:93-100, 2006.
Yla-Herttuala et al., *Arterioscler. Thromb.*, 14:32-40, 1994.
Yla-Herttuala et al., *J. Clin. Invest.*, 84:1086-1095, 1989.
Yla-Herttuala, *Ann. NY Acad. Sci.*, 623:40-59, 1991.
Zhong et al., *Clin. Chem. ACTA.*, 313:147, 2001.
Zou, *Am. J. Epidemiol.*, 159:702-6, 2004.
Zweigenbaum et al., *Anal. Chem.*, 71(13):2294-300, 1999.
Zweigenbaum et al., *J. Pharm. Biomed. Anal.*, 23(4):723-733, 2000.

What is claimed:

1. A method of predicting risk of coronary artery disease (CAD) in a subject comprising:
   (a) providing a modified low density lipoprotein-immune complex (mod-LDL-IC)-containing sample from said subject;
   (b) measuring oxidized-LDL immune complexes (ox-LDL-IC) and/or advanced glycation endproduct-LDL immune complexes (AGE-LDL-IC) in said sample;

(c) comparing the amount of ox-LDL-IC and/or AGE-LDL-IC in said sample to a normal standard; and (d) predicting that said subject is at risk of developing CAD where an elevated amount of ox-LDL-IC and/or AGE-LDL-IC as compared to said standard is observed, or predicting that said subject is at not risk of developing CAD based where an elevated amount of ox-LDL-IC and/or AGE-LDL-IC as compared to said standard is not observed.

2. The method of claim 1, wherein said mod-LDL-IC-containing sample is serum or plasma.

3. The method of claim 1, wherein measuring comprises (i) isolating mod-LDL-IC, (ii) separating mod-LDL from antibodies in said mod-LDL-IC, and (iii) determining ox-LDL and/or AGE-LDL from said mod-LDL-IC levels.

4. The method of claim 3, wherein isolating mod-LDL-IC comprises precipitation.

5. The method of claim 4, wherein separating comprises affinity chromatography of precipitated mod-LDL-IC followed by selective elution of mod-LDL.

6. The method of claim 3, wherein determining comprises capture immunoassay, competitive immunoassay, gas chromatography, mass spectrometry, gel electrophoresis or column chromatography.

7. The method of claim 1, wherein said subject has a family history of CAD.

8. The method of claim 1, wherein said subject exhibits elevated ox-LDL levels.

9. The method of claim 1, wherein said subject exhibits elevated AGE-LDL levels.

10. The method of claim 1, wherein said subject exhibits elevated ox-LDL levels and elevated AGE-LDL levels.

11. The method of claim 1, wherein said subject does not exhibit elevated ox-LDL levels or elevated AGE-LDL levels.

12. The method of claim 1, wherein said subject is male.

13. The method of claim 1, wherein said subject is female.

14. The method of claim 1, wherein said subject is 5 years of age or less.

15. The method of claim 1, wherein said subject is 10 years of age or less.

16. The method of claim 1, wherein said subject is 15 years of age or less.

17. The method of claim 1, wherein said subject is 20 years of age or less.

18. The method of claim 1, wherein said CAD is secondary to type 1 diabetes.

19. The method of claim 1, wherein said CAD is secondary to type 2 diabetes.

20. The method of claim 1, wherein said CAD is secondary to a chronic autoimmune disorder.

* * * * *

UNITED STATES PATENT AND TRADEMARK OFFICE
CERTIFICATE OF CORRECTION

PATENT NO.         : 8,568,995 B2                                         Page 1 of 1
APPLICATION NO.    : 12/885020
DATED              : October 29, 2013
INVENTOR(S)        : Maria F. Lopes-Virella and Gabriel T. Virella It is certified that error appears in the above-identified patent and that said Letters Patent is hereby corrected as shown below:

In the Claims:

In claim 1, column 51, line 6, delete "at not" and replace with --not at-- therefore.

In claim 1, column 51, line 7, delete "based".

Signed and Sealed this
Eleventh Day of February, 2014

Michelle K. Lee
*Deputy Director of the United States Patent and Trademark Office*